(12) United States Patent
Syed Momen et al.

(10) Patent No.: US 8,437,844 B2
(45) Date of Patent: *May 7, 2013

(54) METHOD, SYSTEM AND APPARATUS FOR REAL-TIME CLASSIFICATION OF MUSCLE SIGNALS FROM SELF-SELECTED INTENTIONAL MOVEMENTS

(75) Inventors: Kaveh Syed Momen, Scarborough (CA); Tom Tak Kin Chau, Toronto (CA)

(73) Assignee: Holland Bloorview Kids Rehabilitation Hospital (CA)

( * ) Notice: Subject to any disclaimer, the term of this patent is extended or adjusted under 35 U.S.C. 154(b) by 872 days.

This patent is subject to a terminal disclaimer.

(21) Appl. No.: 11/506,786

(22) Filed: Aug. 21, 2006

(65) Prior Publication Data

US 2008/0058668 A1 Mar. 6, 2008

(51) Int. Cl.
*A61B 5/04* (2006.01)
(52) U.S. Cl.
USPC ............ 600/546; 706/13; 706/14; 706/15
(58) Field of Classification Search ......... 600/587, 600/434, 381, 595, 544–546; 623/24–25, 623/27, 58, 63; 700/213, 250; 706/13, 14; 375/316
See application file for complete search history.

(56) References Cited

U.S. PATENT DOCUMENTS

| | | | | |
|---|---|---|---|---|
| 4,314,379 A * | 2/1982 | Tanie et al. | | 623/25 |
| 5,436,638 A * | 7/1995 | Bolas et al. | | 345/156 |
| 5,724,987 A * | 3/1998 | Gevins et al. | | 600/544 |
| 6,344,062 B1 * | 2/2002 | Abboudi et al. | | 623/24 |
| 6,352,516 B1 * | 3/2002 | Pozos et al. | | 600/587 |
| 6,440,067 B1 * | 8/2002 | DeLuca et al. | | 600/300 |
| 6,785,574 B2 * | 8/2004 | Kajitani et al. | | 600/546 |
| 7,672,717 B1 * | 3/2010 | Zikov et al. | | 600/544 |
| 2001/0014441 A1 * | 8/2001 | Hill et al. | | 434/236 |
| 2002/0143405 A1 * | 10/2002 | Davalli et al. | | 623/24 |
| 2003/0107608 A1 * | 6/2003 | Hong et al. | | 345/863 |
| 2006/0015470 A1 * | 1/2006 | Lauer et al. | | 706/8 |
| 2007/0140562 A1 * | 6/2007 | Linderman | | 382/187 |

OTHER PUBLICATIONS

F. H. Y. Chan, Y.-S. Yang, F. K. Lam, Y.-T.Zhang, and P.A. Parker, "Fuzzy EMG classification for prosthesis control," IEEE Transactions on Rehabilitation Engineering, vol. 8, No. 3, pp. 305-311, Sep. 2000.

S. M. ElBasiouny, A. M. El-Bialy, M. F. Taher,A. H. Kandil, and M. E. Rasmy, "A myoelectric prosthesis controller," in Proceedings of IEEE 29th Annual Bioengineering Conference, Mar. 2003, pp. 140-141.

(Continued)

*Primary Examiner* — Rene Towa
(74) *Attorney, Agent, or Firm* — Katten Muchin Rosenman LLP

(57) ABSTRACT

A new method, system and apparatus is provided that enables muscle signals that correspond to muscle contractions to be mapped to one or more functions of an electronic device such as a prosthetic device or gaming apparatus. Muscle signals are classified in real-time from self-selected intentional movements. A self-training protocol allows users to select and label their own muscle contractions, and is operable to automatically determine the discernible and repeatable muscle signals generated by the user. A visual display means is used to provide visual feedback to users illustrating the responsiveness of the system to muscle signals generated by the user.

35 Claims, 18 Drawing Sheets

OTHER PUBLICATIONS

B. Karlik, M. O. Tokhi, and M. Alci, "A fuzzy clustering neural network architecture for multifunction upper-limb prosthesis," IEEE Transactions on Biomedical Engineering, vol. 50, No. 11, pp. 1255-1261, Nov. 2003.

D. Nishikawa, W. Yu, H. Yokoi, and Y. Kakazu, "On-line learning method for EMG prosthetic hand control," Electronicsand Communications in Japan, Part 3, vol. 84, No. 10, pp. 1510-1519, Nov. 2001.

K. Englehart, B. Hudgins, and P.A. Parker, "A wavelet-based continuous classification scheme for multifunction myoelectric control," IEEE Transactions on Biomedical Engineering, vol. 48, No. 3, Mar. 2001.

D. Peleg, E. Braiman, E. Yom-Tov,and G. F. Inbar, "Classification of finger activation for use in a robotic prosthesis arm," IEEE Transactions on Neural Systems and Rehabilitation Engineering, vol. 10, No. 4, pp. 290-293, Dec. 2002.

N. Ma, D. K. Kumar, and N. Pah, "Classification of hand direction using multi-channel electromyography by neural network," in The Seventh Australian and New Zealand 2001 Intelligent Information Systems Conference, Nov. 2001, pp. 405-410.

H.-P. Huang, Y.-H. Liu, and C.-S. Wong, "Automatic EMG feature evaluation for controlling a prosthetic hand using supervised feature mining method: an intelligent approach," in Proceedings of the 2003 IEEE International Conference on Robotics and Automation, vol. 1, Taipei, Taiwan, Sep. 2003, pp. 220-225.

H.-P. Huang, Y.-H. Liu, L.-W. Liu, and C.-S. Wong, "EMG classification for prehensile postures using cascaded architecture of neural networks with self-organizing maps," in Proceedings of the 2003 IEEE International Conference on Robotic and Automation, vol. 1, Taipei, Taiwan, Sep. 2003, pp. 1497-1502.

K. Englehart and B. Hudgins, "A robust, real-time control scheme for multifunction myoelectric control," IEEE Transactions on Biomedical Engineering, vol. 50, No. 7, pp. 848-854, Jul. 2003.

K. Englehart, B. Hudgins, and A. D. Chan, "Continuous multifunction myoelectric control using pattern recognition," Technology and Disability, vol. 15, pp. 95-103, 2003.

M. Vuskovic and S. Du, "Classification of prehensile EMG patterns with simplified fuzzy ARTMAP networks," in Proceedings of the 2002 International Joint Conference on Neural Networks, IJCNN '02, vol. 3, Honolulu, HI, May 2002, pp. 2539-2544.

Y. Yazama, M. Fukumi, Y. Mitsukura, and N. Akamatsu, "Feature analysis for the EMG signals based on the class distance,"in Proceedings of the 2003 IEEE International Symposium on Computational Intelligence in Robotics and Automation, vol. 2, Kobe, Japan, Jul. 2003, pp. 860-863.

Y. Matsumura, Y. Mitsukura, M. Fukumi, and N. Akamatsu, "Recognition of EMG signal patterns by neural networks,"in Proceedings of the 9th International Conference on Neural Information Processing, vol. 2, Nov. 2002, pp. 750-754.

M. Santa-Cruz, R. Riso, and F. Sepulveda, "Optimal selection of time series coefficients for wrist myoelectric control based on intramuscular recordings," in Proceedings of the 23rd Annual International Conference of the IEEE Engineering in Medicine and Biology Society, vol. 2, Istanbul, Turkey, Oct. 2001, pp. 1384-1387.

R. Boostani and M. H. Moradi, "Evaluation of the forearm EMG signal features for the control of a prosthetic hand," Physiological Measurement, vol. 24, No. 2, pp. 309-319, May 2003.

K. Englehart, B. Hudgins, P. Parker, and M. Stevenson, "Classification of the myoelectric signal using time-frequency based representations," Medical Engineering & Physics, vol. 21, No. 6-7, pp. 431-438, Jul. 1999.

X. Zhang, Y. Yang, X. Xu, and M. Zhang, "Wavelet based neuro-fuzzy classification for EMG control," in IEEE 2002 International Conference on Communications, Circuits and Systems and West Sino Expositions, vol. 2, Jul. 2002, pp. 1087-1089.

S. E. Hussein and M. H. Granat, "Intention detection using a neuro-fuzzy EMG classifier," IEEE Engineering in Medicine and Biology Magazine, vol. 21, No. 6, pp. 123-129, Nov.-Dec. 2002.

J. C. Bezdek, Pattern Recognition with Fuzzy Objective Function Algorithms. Plenum Press, New York, 1981.

N. R. Pal and J. C. Bezdek, "On cluster validity for the fuzzy c-means model," IEEE Transactions on Fuzzy Systems, vol. 3, No. 3, pp. 370-379, Aug. 1995.

C. J. DeLuca, "The use of surface electromyography in biomechanics," Journal of applied Biomechanics, vol. 13, pp. 135-163, 1997.

J. V. Basmajian and C. J. Deluca, Muscles Alive, their functions revealed by electromyography, 5th ed. Williams.

B.S. Hudgins, P.A. Parker and R.N. Scott, A new strategy for multifunction myoelectric control, IEEE Transactions on Biomedical Engineering 40(1) (1993), 82-94.

A. B. Ajiboye, R. F Weir, A Heuristic Fuzzy Logic Approach to EMG Pattern Recognition for Multifunctional Prosthesis Control, IEEE Transactions on Neural systems and Rehabilitation Engineering, vol. 13, No. 3, Sep. 2005.

F. Sebelius, L. Eriksson, H. Holmberg, A. Levinsson, G. Lundborg, N. Danielsen, J. Schouenborg, C. Balkenius, T. Laurell, L. Montelius, Classification of motor commands using a modified self-organising feature map, Medical Engineering & Physics 27 (2005) 403-413.

Y. Huang, K. B. Englehart, B. Hudgins, A. D. C. Chan, A Gaussian Mixture Model Based Classification Scheme for Myoelectric Control of Powered Upper Limb Prostheses, IEEE Transactions on Biomedical Engineering, vol. 52, No. 11, Nov. 2005.

C. Orizio, D. Liberati, C. Locatelli, D. DeGrandis, A. Veicsteinas A. Surface mechanomyogram reflects muscle fibres-twitches summation, Journal of Biomechanics 29 (4): 475-481 Apr. 1996.

J. G. Proakis and D. G. Manolakis. Digital Signal Processing: Principles, Algorithms and Applications. Prentice Hall, third edition, 1996.

D. W. Scott. Multivariate Density Estimation. John Wiley & Sons Inc., New York, 1992.

\* cited by examiner

METHOD, SYSTEM AND APPARATUS FOR REAL-TIME CLASSIFICATION OF MUSCLE SIGNALS FROM SELF-SELECTED INTENTIONAL MOVEMENTS

FIELD OF THE INVENTION

The present invention relates to a method, system and apparatus for classifying muscle signals. More particularly, the present invention relates to a method, system and apparatus for mapping muscle signals to one or more functions of an electronic device.

BACKGROUND OF THE INVENTION

References to background documents refer to items on the "List of References" below.

Externally powered prosthetic hands are typically controlled using electromyographic (EMG) signals. These signals originate from the polarization and depolarization of the muscle membrane during voluntary contractions and can be measured at the skin surface using either dry or wet-type electrodes. The EMG control signal can be derived from a single site [References 1, 2, 3] or from multiple sites. Past studies have employed two [Reference 4, 5, 6], three [References 7, 8, 9], four [References 5, 10, 11, 12, 13, 14, 15], and up to eight [Reference 16] recording sites with varying levels of success. Englehart and Hudgins argued that four channels of EMG signals are clearly preferable to two [Reference 5]. However, some studies have shown that there is both a practical and theoretical limit to increasing the number of channels [References 10, 5].

MMG Versus EMG

Generally speaking, EMG is a measure of the electrical activity of skeletal muscle. It arises from the successive polarization and depolarization of the muscle membrane. Surface EMG is a temporal and spatial summation of elemental motor unit action potentials.

Muscles vibrate at low frequencies upon contraction. The superficial measurement of these vibrations is known as the mechanomyogram (MMG). The MMG signal originates from the summation of propagated active muscle fibre twitches [Reference 28].

While EMG measures electrical activity, MMG reflects the mechanical activity of the muscle. Hence, EMG and MMG are measuring different but complementary phenomena that accompany muscle contraction.

Static EMG Classifiers

A much sought after goal in EMG-driven prostheses is to provide the user with multiple limb functions, such as hand opening and closing, and wrist rotation. To control multiple functions, it is necessary to map EMG signals corresponding to different muscle contractions to a variety of prosthetic functions. This mapping is commonly achieved by way of a signal classification scheme. In the past decade, many different EMG classification schemes have been proposed for prosthesis control. These classifiers can be divided into four major categories.

Linear classifiers, such as linear discriminant functions, assume that the different classes of contractions are linearly separable [References 10, 5, 17, 2]. Although the linearity assumption would appear limiting, the cited studies have reported competitive performance results, perhaps partly due to the prudent choice of signal features.

Artificial neural network (ANN) classifiers, such as the standard workhorse multilayer feed forward network, can model general nonlinear boundaries among contraction classes [References 1, 4, 6, 7, 3, 8, 9, 11, 13, 14]. Due to this nonlinear capability and robustness to noisy data, these classifiers have been the preferred choice in the vast majority of recent studies. Typically, however, a sufficiently large data set is required to adequately train such networks.

Fuzzy and neuro-fuzzy classifiers deploy combinations of fuzzy coding schemes and nonlinear class modeling of neural networks [References 1, 18, 19, 25]. While not as prevalent as the previous classifier genre, these methods also admit potential nonlinear class boundaries.

K-nearest neighbour EMG classifiers build on the classical nonparametric algorithm by the same name, which is known to be asymptotically Bayes optimal [References 6, 8]. As the computational requirement per classification of a k-nearest classifier is large relative to the aforementioned methods, there have been very few real-time considerations of this genre of classifiers.

The number of recording sites in past EMG classification systems has mostly varied from 1 to 4. Classification accuracies ranging from 80% to 100% have been reported using ANN classifiers for 4 to 8 different functions. Sebelius et. al. [Reference 26] in a recent study found that modified self-organizing feature map (SOFM) composed of a combination of a Kohonen network and the conscience mechanism algorithm (KNC) was superior in performance to the reference networks, such as multi-layer perceptrons, as regards training time, low memory consumption, and simplicity in finding optimal training parameters and architecture. By applying this method on EMG signals, recorded from 8 sites on an amputee and an able-bodied subject, they could classify six movements out of seven with 100% accuracy. It was found that a KNC network comprising 25 nodes was sufficient to classify the hand movements. The network training was completed after 500 repetitions.

Huang et. al. [Reference 27] used a Gaussian Mixture Model (GMM) based classifier to classify 6 predefined hand movements, using 4 EMG channels. The signals were recorded from 12 able-bodied subjects. The data used in this work were the same as those used in previous investigation by the authors [Reference 11]. Autoregressive coefficients+root-mean-square feature vector was found to be the best feature vector in this application. The performance of GMM was compared to three commonly used classifiers: a linear discriminant analysis, a linear perceptron network, and a multi-layer perceptron neural network. The GMM based classifier demonstrated exceptional classification accuracy and resulted in a robust method of motion classification with low computational load. The performance of the system on limb deficient subjects is currently being investigated.

It has been suggested that without the capability to dynamically update over time, the discrimination rate of such majority of aforementioned classifiers would drop to about 60% over the course of actual usage [Reference 4]. It is generally not obvious how previously reported classifiers may be adapted dynamically to accommodate daily variations in EMG signals, due for example, to fatigue.

Dynamic EMG Classifiers

Although most of these methods have only been tested off-line, a few real-time algorithms have been proposed. Englehart et al. [Reference 10] used a pattern recognition approach to process four channels of myoelectric signal, with the task of discriminating four classes of limb movement, based on the "continuous classifier", introduced in their earlier studies [Reference 5]. Twelve subjects with intact upper limbs participated in the study. The subjects were instructed to perform wrist flexion, wrist extension, radial deviation and ulnar deviation with moderate force. A linear discriminant analysis (LDA) classifier was used in this study. One half of the data was used to train the LDA classifier, and the other half was used as a test set to evaluate the classifiers accuracy.

In a subsequent work, Englehart et. al. [Reference 11] processed four channels of myoelectric signal, with the task of discriminating six classes of limb movement. The training session was strictly divided into the trial consisting of transient data, and the trial consisting of continuous contractions. The main drawback however, of using the transient myoelectric signal as a control input was that it required initiating a contraction from rest. This prohibited switching from class to class in an effective or intuitive manner. It severely impeded the coordination of complex tasks involving multiple degrees of freedom. Therefore, pattern recognition of continuous contraction (steady state signal) was also considered. Eleven subjects with intact limbs participated in the study. The subjects were asked to perform six predetermined limb motions namely, wrist flexion, wrist extension, supination, pronation, palm open, and palm close. Subjects performed two trials as part of this experiment: the first trial consisting of transient data, and the second trial consisting of continuous contractions. In the first trial, subjects were asked to perform rapid contractions, producing 40 burst patterns for each of the six classes, with each burst pattern being 256 samples (256 ms) in length. This was then repeated again to create a second set of patterns. The first set of 6×40=240 patterns was used as a training set, and the second set of 240 patterns used as the test set. In the second trial, subjects underwent four, 60 seconds sessions, producing continuous contractions. Within each session, subjects held each limb motion twice, for a five second duration. The first and third session were used as training sessions. During training sessions, the six limb motions were performed twice, in the order: wrist flexion, wrist extension, supination, pronation, palm open, and palm close. These were performed in response to a computer-generated prompt. These remaining two sessions were used as test sets. In these sessions, each limb motion was also repeated twice but the order of the limb motions was randomized. The transient and continuous data were subject to classification using five different feature sets:

1. the time-domain features [Reference 24];
2. short-time Fourier transform (STFT) coefficients, using a hamming window, 32 ms segments, overlapping by 50%;
3. wavelet transform (WT) coefficients, using a Coiflet-5 mother wavelet;
4. wavelet packet transform (WPT) coefficients, using a Symmlet-5 wavelet and a local discriminant basis algorithm to determine the basis; and
5. Stationary wavelet transform (SWT) coefficients.

They obtained an impressive 93.25% accuracy using a time-domain feature set, with a multilayer perceptron (MLP) artificial neural network classifier. Although the study only enlisted able-bodied individuals who could perceive the requested predefined movements, future tests with individuals with upper limb deficiencies were to be investigated.

In a separate study, Nishikawa et al. [Reference 4] proposed a novel on-line learning method for discriminating six different predetermined hand movements, namely supination, pronation, flexion, extension, grasping, and opening. They used two electrode channels, which were placed on the inside and the outside of the wrist. However, it is not clear how these locations on the wrist represented the agonist and antagonist muscle groups on the forearm, which are responsible for hand movements. They used a method that had structural similarities to the adaptive heuristic critic (AHC). The AHC generates an inner evaluation signal from external reinforcement signals and input, after which the AHC learns from the inner evaluation signal. This system had three main units:

Analysis unit: This was responsible for extracting the features. In this experiment Gabor transform, which is a discrete Fourier transform using a Gaussian window, was used to generate the feature vector. The interpolation process was used to smooth out the shape of the spectrum.

Adaptation unit: A feed-forward artificial neural network (ANN) was used to realize the Adaptation Unit. This section received the feature vectors from the user, and tried to map them to the desired output.

Trainer unit: The Trainer Unit sent the training data to the Adaptation Unit in order, and updated the inner state of this unit. In order to avoid over learning, Root-mean-square of the teaching signals were calculated and were compared to a predetermined threshold. This served as a prompt for the adaptation unit to either start or stop learning from the training section.

Although they could discriminate six different forearm movements with 89.9% accuracy, training the prosthetic hand required predetermined movements (subjective judgment). When a subject judged that the system could control a motion intentionally, he taught the hand a new motion, thus directing system learning. On the other hand, when the subject judged that the system was unable to control a motion properly, he had to retrain the motion in question and the system needed to relearn all the target motions. Therefore, the training of the prosthetic hand and adaptive capability were not automatic.

Ajiboye and Weir [Reference 25] used a heuristic fuzzy logic approach to multiple EMG pattern recognition for multifunctional prosthesis control. Heuristics is a computational method that uses trial and error methods to approximate a solution for computationally difficult problems. The task was to classify four different forearm movements in able-bodied subjects, such as wrist extension, wrist flexion, ulnar deviation and finger flexion. The location of the electrode sites were carefully chosen by a trained prosthetist according to the standard clinical practice (four sites for able-bodied, three sites for amputees), and these sites were prepared by shaving any excessive body hair in the site region to maximize physiological separability between signals. The ratio between the number of EMG channels and number of expected movements was considered one. The subject with trauma-induced limb deficiency (Subject A), was not able to perform supination, and the subject with congenital limb deficiency (Subject C) was not able to perform pronation properly. Therefore, based on the ability of the amputee subjects, only three independent surface sites were chosen to classify three different forearm movements. Eight trials were performed by each subject. All contractions were performed at a speed and strength determined by the subject. The actual classification was done offline, by choosing the odd numbered trials as training sets. The real-time experienced was performed on an able-bodied subject, who was believed to be the best-case scenario, as he possessed a full independent control over the motions of interest and was able to obtain adequate physiological separation of EMG signals. A 45.7 millisecond window was chosen to calculate the features. They used mean and standard deviation of the signal for membership function construction, and fuzzy c-means (FCMs) data clustering was used to automate the construction of a simple amplitude-driven inference rule base. With a little bit of tweaking, overall classification rates ranged from 94% to 99%. The fuzzy algorithm also demonstrated success in real-time classification, during both steady state motions and motion state transitioning. Unfortunately, the algorithm was not tested on subjects with limb deficiency in real-time. It also appears that the ability of the subjects to produce self-selected movements was ignored. For example, as discussed earlier, the subjects with limb deficiency were estimated to perform three predefined movements based on their ability to produce forearm movement according to the generally accepted social norms (extension, flexion, and supination (subject C) or pronation (subject A). However, these subjects may be able to produce more movements, which are perceivable to them.

There are several notable patents relevant to the field of the present invention.

U.S. Pat. No. 4,209,860 to Graupe teaches time series modeling, so called "Autoregressive Coefficients" modeling, to model the specific EMG signal produced by a specific movement. As for classification, the method compares the current produced EMG signal with the saved model. It is not clear how the system is trained. However, it was mentioned the calibration was done clinically. This presumably would involve significant user training, and therefore Graupe does not provide a method and prosthetic device wherein the training and adaptive capability is automatic.

U.S. Pat. No. 4,314,379 to Tanie discloses using amplified, rectified, filtered EMG signals from four sites. However, it is mentioned that the number of inputs and outputs can be fixed freely. In accordance with that invention, the user was asked to perform certain movements several times. The results are then averaged these results and these features are fixed in the memory. The upcoming movements would be classified using Linear Discriminant Analysis (LDA), based on the training sets. In this approach the user is restricted to perform certain movements over time, i.e. as part of supervised learning. As for training, it is not clear how many times the user had to train the system and how successfully they could classify movements based on the training data. Apparently, the system could not adaptively change its state over time.

Further, U.S. Pat. No. 6,254,536 to DeVito is an example of systems which are controlled by physiological signals, mainly EEG (brainwaves) and EMG (for monitoring eye movements). The systems include three electrodes in contact with the subject's forehead to pick up the EEG signals. Due to the location of the electrodes on the forehead, brainwave activity (EEG), eye movement and muscle movement (EMG) are all monitored through the same electrodes. It is well known that the frequency band of EEG signals correlates with the state of the brain activity.

For example, alpha wave forms which are usually seen in 8-12 Hz band, show that the subject is relaxed, and high beta wave forms (higher than 18 Hz) show a subject's intensive thinking, such as performing mathematical calculations. In this study, Fast Fourier Transform (FFT) was used to calculate different properties of the signals, and to estimate the state of the brain activity. Passive and active interaction with various electronic media such as video games, movies, music, virtual reality, and computer animations was also disclosed.

U.S. Pat. No. 6,785,574 to Kajitani et al. discusses six predefined actions (forearm pronation, forearm supination, wrist flexion, wrist extension, hand closing and hand opening) to be classified using four sets of electrodes. The subjects were instructed to initiate a 3 second continuous contraction period, followed by a 2 second relaxation period twenty times for each of the six actions. They extracted features while the muscle contraction was maintained (steady state EMG). They set the point when the sum of all EMG signal recorded from four sites, exceeded a pre-determined threshold, which marked the initiation of the contraction. This point served as a time stamp for transient EMG initiation. They waited one second, followed by another 100 milliseconds, to start averaging the steady state EMG signal for each channel. This period of averaging lasted for 1 second. Then, ten averaged values for one muscle contraction were calculated by average the EMG signal over the same period, each shifted and overlapped by 100 milliseconds. These rectified, amplified, filtered signals were subject to logarithmic transformation to get a better resolution, for each channel. However, in practice, depending on how a muscle contracted, there were cases in which the total value of EMG signals did not exceed the preset threshold value. Therefore, not all the twenty training contractions per action could be used as training patterns. On the other hand, setting a threshold is quite subjective. Setting this threshold too low makes the system actuation susceptible to noise, and setting it too high, makes the system not responsive to the EMG actuation. Therefore, the system may not respond to the initiated EMG signals properly and as a result, controlling the powered prostheses, which work based on these algorithms, may become frustrating for the user.

In U.S. Pat. No. 6,859,663 to Kajitani et al., the inventors build on the method taught by U.S. Pat. No. 6,785,574 (referenced directly above) by using redundant coding to encode feature patterns into bit patterns. With respect to arbitrary consecutive values the redundant code always differs by just one bit, differs by two bits when the difference is 2, and differs by three bits when the difference is 3, making it possible to realize a classification circuit with a simple circuit. A circuit that performs high-speed execution of a search technique called a genetic algorithm was used to adaptively rewrite the circuit configuration. Although it was argued that this technique on averaged improved the classification rate by 3.1%, and the required time for circuit synthesis was reduced by 69.6%, the actual accuracy results were not reported. It is also unclear how this method may be beneficial for subjects with limb deficiency in real-time applications. This patent simply provides another example of EMG classification, based on the inventors earlier work in U.S. Pat. No. 6,785,574.

In U.S. Pat. No. 6,272,479 to Farry et al., the inventors argued that the technical problem common to all the reviewed background art in this area was that no program or system provided a reliable and repeatable output when presented with an input signal or signals having features that were not well characterized or linearly separable or separable on a single feature. They solved this problem utilizing an "evolver" program to examine a large number of potential features, which may be from multiple signals to create a "classifier" program. They investigated the following features:

1. mean absolute value (MAV);
2. MAV slope between time intervals;
3. energy;
4. rate of change of energy;
5. average value;
6. number of zero crossings;
7. number of up slopes;
8. number of down slopes;
9. waveform complexity;
10. mean frequency;
11. median frequency;
12. energy or power at any frequency;
13. variance; and
14. autoregressive or autoregressive moving average parameters; and ratios or other combinations of the above.

The output of the classifier program was compared to the desired output. One or more classifier programs was then created and optimized by the evolver program by means of genetic programming. The desired output was again compared to actual classifier program output and the difference was used as a measure of fitness to guide the evolution of the classifier program. The algorithm required identifying the start command (either manually by the user or automatically by a preset threshold). Then the system tried finding the best possible features and recording sites by means of genetic programming. In real-time implementation, it was suggested that the user should inform the algorithm of any errors by pressing a push button. If the number of errors exceeded a preset value, the algorithm had to retrain itself. There is no indication of the success rate of the proposed algorithm in a real-time application for either limb deficient or able-bodied subjects. Further, it should be noted that this method may or may not converge to the best solution. Genetic programming requires thousands of iterations to search for the both best feature sets and the best classifier function. This process is not usually very fast and requires substantial memory and processing resources.

In addition to the shortcomings mentioned above, there are several other general drawbacks to the previous approaches, which are evident to a person skilled in the art.

In particular, most of the past research and development efforts have been carried out only with able-bodied subjects and not amputees. However, we know that there are significant anatomical and physiological differences between the amputated and intact limb. For example, in congenital amputees, there may be partially developed, missing or fused bones. The soft tissue is commonly heavier or thicker than in the intact limb. In the traumatic amputee, the limb may exhibit scarring, grafted skin areas, muscle atrophy and limited range of motion. As a result, the number of available muscle sites and the quality of useful EMG signals may be very different from those of the intact limb, implying that potentially different EMG features and classifiers may be required.

Further, current devices require users to perform activities according to the generally accepted social norms for executing the target activity. For example, flexion of the forearm muscles is typically associated to prosthetic hand closing. However, these normative modes of activity execution may not be natural for the user and often do not make best use of the individual's abilities. Consequently, effective device usage requires significant user training. It also appears that in most previous approaches, the ability of the subject to express functional intent was also ignored. For instance, the subject would be asked to perform predefined different hand movements, i.e. hand close, hand open, finger movement, etc. which are meaningful for able-bodied subjects but meaningless for amputees, especially those that have congenital limb deficiencies.

In addition, the prior art discloses that pre-processing of EMG signal was necessary. For example, in order to define the start of a specific movement, by examining an EMG signal, a threshold was predefined. For instance, if power of an EMG signal exceeded the threshold, the system would take this point as the time when the movement was initiated. Unfortunately, setting a threshold is quite subjective. Setting this threshold too low makes the system actuation susceptible to noise, and setting it too high, makes the system unresponsive to the EMG actuation. It may be possible to define this threshold by trial and error in a lab, but it is not possible to set this dynamically, as the skin condition (skin perspiration) and other physiological properties of the muscle changes over time, for example, due to fatigue. Therefore, the system may not respond to the initiated EMG signals properly, and as a result, the use of these devices, for example, powered prostheses, becomes frustrating for the user.

Finally, in almost all of the previous approaches, different movements were classified using supervised classifiers (i.e. Artificial Neural Networks). Hence, correct partitioning of the feature space required accurately labelled movements. Such movements could only be obtained according to a strict experimental protocol. In other words, users could not freely generate movement of choice, but had to adhere to the experiment's instruction. Past research often employed pre-recorded EMG databases. The data sets for learning were part of the data sets for verification. These data were recorded with specific electrodes, skin conditions, electrode locations, soft tissue composition, and muscle anatomy. Good performance of the supervised classifiers could only be guaranteed under similar experimental conditions. In other words, to verify the discrimination ability under conditions closer to practical use, the data for verification must be measured and generated after measurement of the data for learning. It has been reported that [Reference 4] if the learning system did not alter its inner state dynamically, the discrimination rate dropped to about 60% in the course of time. On the other hand, ANN classifiers require a great number of samples to train the network. This implied the higher number of training samples. There is also a problem of overtraining the network, which may affect the accuracy of the network. Similarly, genetic programming, used in U.S. Pat. Nos. 6,272,479 and 6,859,663, requires the algorithm to run a great number of times to evaluate thousands of evolutions, which at the end may not converge to the desirable answer. The success of these algorithms greatly depends on the choice of the features and functions. Therefore, these algorithms may not be suitable to be implemented into an embedded system. It is also not clear how fast these algorithms may adaptively change their inner state in embedded real-time applications, where there are limited resources for memory and processing power. Unfortunately, there is no report on the successful implementation of these algorithms on a portable (embedded) system.

What is needed is a method, system and apparatus for classifying muscle signals that overcomes the shortcomings of the prior art.

SUMMARY OF THE INVENTION

The present invention is a new method, system and apparatus that enables muscle signals that correspond to muscle contractions to be mapped to one or more functions of an electronic device such as a prosthetic device or a gaming apparatus.

In accordance with the present invention, muscle signals are classified in real-time from self-selected intentional movements. It should be understood that the muscle signals can be either EMG or MMG signals, in accordance with the present invention.

In a particular aspect of the present invention, a self-training method, system and apparatus is provided that enables muscle signals to be mapped to one or more prosthetic functions, whereby a users select and label their own muscle contractions through a self-training protocol. In accordance with the self-training protocol, instead of manually identifying target motions, such as "hand close", "hand open", "supination", "pronation", etc., the present invention learns from the user's self-selected intentional movements. Specifically, the self-training protocol is operable to automatically determine the discernible and repeatable muscle signals generated by the user. The user can then choose the preferred assignment of muscle activity to the one or more prosthetic functions. In this way, user training can be minimized.

The present invention should also be understood as a means of calibrating a prosthetic device, and one or more prosthetic functions associated with the prosthetic device, to one or more discernible and reproducible muscle signals generated by a user.

The system of the present invention, in another aspect thereof, comprises a prosthetic device, a computer linked to the prosthetic device, and computer programming loaded on the computer that enables the self-training functionality of the present invention. In a particular aspect of the system of the present invention, a visual display means is used to provide visual feedback to users illustrating the responsiveness of the system to muscle signals generated by the user.

The apparatus of the present invention, in one aspect thereof, comprises a prosthetic device incorporating the self-training functionality of the present invention. In another aspect thereof, the apparatus of the present invention comprises a controller for use in a prosthetic device, the controller incorporating a self-training routine in accordance with the present invention. In yet another aspect thereof, the apparatus of the present invention comprises a computer program that when loaded on a computer linked to a prosthetic device enables the prosthetic device to be calibrated based on a self-training routine in accordance with the present invention. In a still other aspect of the present invention, the apparatus of the present invention comprises a control program that is operable on a controller included in a prosthetic device, wherein the control program implements a self-training routine in accordance with the present invention.

The method, system and apparatus of the present invention are particularly directed at an improved design of upper extremity prostheses, which are user independent and can operate based on a user's self-selected functional intent.

As stated earlier, the present invention enables a prosthetic device to be calibrated by mapping discernible and reproducible muscle signals of a particular user to one or more functions of the prosthetic device. Rather than requesting users to perform activities according to norms for executing a target activity (which may not apply, or may apply to a varying degree, to particular users), or to generate a muscle signal that meets a particular threshold (which may not apply, or may apply to a varying degree, to particular users), the present invention operates on the basis of analysis of a range of discernible and reproducible muscle signals that a particular user is capable of generating.

The muscle signals are then processed to extract features from the signals associated with the muscle signals, which can be accomplished using a suitable feature extractor means. In a preferred embodiment of the present invention, the features are extracted by calculating the natural logarithm of root-mean-square values. These features then define a feature space, which can be subsequently clustered using a suitable clustering algorithm. In an aspect of the preferred embodiment, fuzzy c-means clustering algorithm can be used. The foregoing feature extraction/clustering/classification means is suited to real-time applications where the computation complexity is constrained.

In a particular aspect of the invention, the algorithm used is operable to determine membership values of each point to classify the movements. It can also be dynamically adaptive, to automatically adapt to daily variations in individual muscle signals. The process of feature extraction and classification is very easy and fast so that this algorithm is suitable for embedded real-time applications.

As stated earlier, instead of manually identifying target motions, such as "hand close", "hand open", "supination", "pronation", etc., which are perceivable by able-bodied subjects but meaningless to the users with limb deficiency, the present invention learns from the user's self-selected intentional movements. Therefore, the learning is shifted from the user to the machine and the user training can be minimized. The self-training protocol is also operable to automatically determine the discernible and repeatable muscle signals generated by the user.

The present invention therefore improves the ability to connect functional intent of a user to electronic functions of an apparatus such as a prosthetic device or a gaming device. This provides better operation of such devices, from a user perspective. The fact that the method described is self-training, for example provides savings of the time of health care professionals involved in calibration of prosthetic devices and training of their users, over conventional techniques. The self-training aspect of the present invention contributes to a sense of control of users over the use of their prosthetic device, which in turn contributes to satisfaction of users with their prosthetic device overall.

Another aspect of the present invention is that the self-training method can be readily applied dynamically to address changes in individuals' muscle signals over time, and making necessary adjustments to the mapping of device functions. This permits maintenance of optimal performance of the prosthetic device with little or not involvement of health care professionals, for example, in the case of a prosthetic. Accordingly, an electronic device such as a prosthetic device in accordance with the present invention is "self-maintaining", which further contributes to user satisfaction. Further, the self-training aspect enables calibration of devices in a way that it reduces the potential for language or comprehension barriers.

Another aspect of the present invention, although skin preparation may result in a better performance, no skin preparation is necessary because a device is calibrated based on the current user's skin condition and, consequently, the algorithm is robust to skin conditions. This may help the clinicians to fit the prostheses more quickly.

In a further aspect of the present invention, a gaming apparatus is provided, wherein the gaming apparatus includes the self-training functionality of the present invention for mapping muscle signals to one or more gaming functions of the gaming apparatus.

BRIEF DESCRIPTION OF THE DRAWINGS

FIG. 3($b$) illustrates a logarithmic plot of calculated RMS features from the extensor muscles versus the calculated RMS features from the flexor muscles for a 200-millisecond window.

FIG. 4($b$) illustrates an example of a user interface for visual feedback.

FIG. 4($c$) illustrates an example of a user who is using the visual feedback as a response to his forearm movements.

Figure 1:
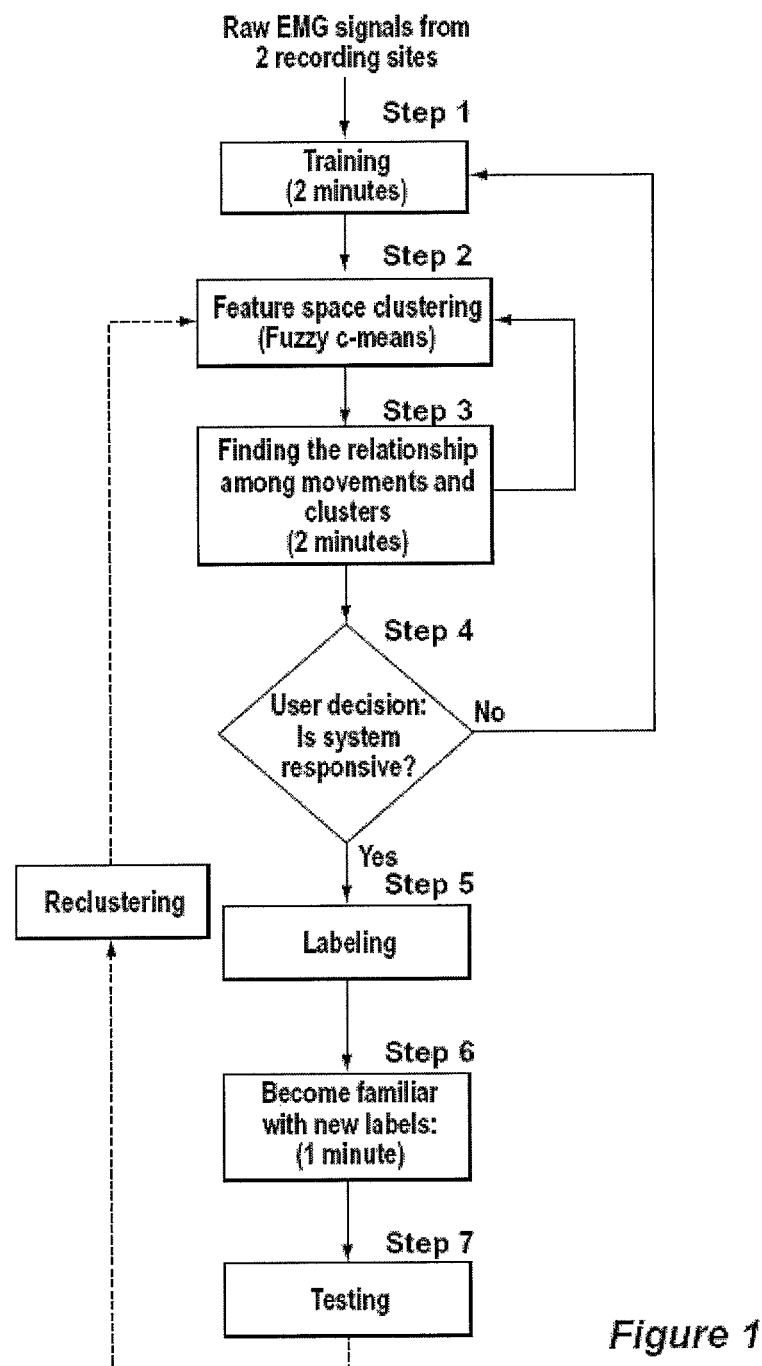
FIG. 1 illustrates a summary of a protocol method of constructing a real-time classifier exploiting user-selected and labelled movements.

In the drawings, one embodiment of the invention is illustrated by way of example. It is to be expressly understood that the description and drawings are only for the purpose of illustration and as an aid to understanding, and are not intended as a definition of the limits of the invention.

DETAILED DESCRIPTION OF THE INVENTION

The present invention is a new method, system and apparatus that enables muscle signals that correspond to muscle contractions to be mapped to one or more functions of an electronic device, such as a prosthetic device or a gaming apparatus, by classifying the signals in real-time from self-selected intentional movements. As mentioned, the present invention is particularly directed at an improved design of upper extremity prostheses, which are user independent and can operate based on a user's self-selected functional intent.

The method applies to any device where it is desirable to enable a user to control the device functions by means of muscles signals. For example, in addition to prosthetic devices, the present invention extends to gaming apparatus or any input device, e.g. a modified mouse.

It should be understood that the muscle signals can be either EMG or MMG signals, in accordance with the present invention. While specific implementations herein may refer to EMG, the present invention is operable for MMG muscle signals, as discussed below.

As stated earlier, the present invention enables a prosthetic device to be calibrated by mapping discernible and reproducible muscle signals of a particular user to one or more functions of the prosthetic device. Instead of requesting users to perform activities according to norms for executing a target activity (which may be difficult and sometimes impossible for a particular user to perform), or to generate a muscle signal that meets a particular threshold (which a particular user may not be able to achieve), the present invention operates on the basis of analysis of a range of discernible and reproducible muscle signals that a particular user is capable of generating. The natural logarithm of root-mean-squared values of the muscle signals is calculated to create a feature space. The feature space, which contains the training data, is then clustered. Fuzzy c-means, which is an example of a clustering algorithm, is used in this invention to cluster the feature space and the membership values of each data point in the feature space is used to classify the muscle signal. The membership value of each point can be simply considered as a distance measure from each data point to the cluster center, which can be easily calculated. This is suited to real-time applications where the computation complexity is at a reasonable level.

Therefore, the present invention improves the connection of a user's functional intent and the electronic functions of an apparatus, such as a prosthetic device or a gaming device.

This provides for the better operation of such devices, from a user's perspective. The self-training aspect of the present invention is advantageous, for example by reducing the time of health care professionals required for calibration of prosthetic devices and training of their users, over conventional techniques. This contributes to a sense of control of users over the use of their prosthetic device, which in turn contributes to satisfaction of users with their prosthetic device overall.

Method

The overall method for constructing a real-time classifier exploiting user-selected and labelled movements is summarized in FIG. 1.

Figure 2:
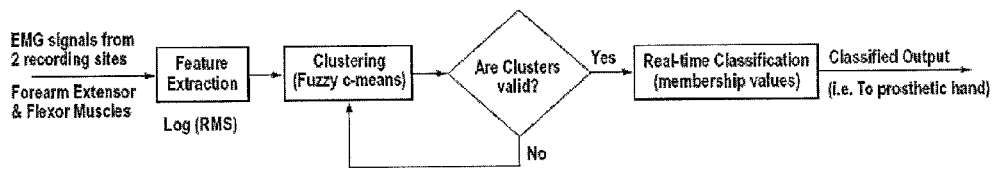
FIG. 2 illustrates a summary of feature extraction, clustering and classification aspects of the present invention.

The present invention differs from previous approaches in the choice of the feature sets, clustering and classification method, and training protocol. These steps are summarized in FIG. 2. In the present invention, natural logarithms of root-mean-square values of EMG signals are calculated. The user trains the system by producing any self-selected movements. Then the created feature space is clustered using a fuzzy clustering algorithm, and the new data points will be assigned to the corresponding cluster by calculating the membership value, discussed below. The logarithmic transformation is performed on the filtered RMS values of EMG signals over a window equal or less than 200 milliseconds. Advantageously, the present invention does not require any preset EMG signal threshold, and skin preparation is not necessary as the algorithm learns the movements from the current skin and environmental noise conditions, and adapts its inner state with the user's signal variations, over time. For clustering the feature space, which contains the training data, a clustering algorithm, such as fuzzy c-means, which is an unsupervised classifier, is used, and fuzzy membership values of the features, helped to classify the, movement in real time. The training time is much faster than previous approaches, as the algorithm learns from the user's self-selected intentional movements.

The self-training aspect is also advantageous in that the method is readily applied dynamically to address changes in individuals' muscle signals over time, and making necessary adjustments to the mapping of device functions. For example, this permits maintenance of optimal performance of the prosthetic device with little or not involvement of health care professionals. Accordingly, an electronic device such as a prosthetic device in accordance with the present invention is "selfmaintaining", which further contributes to user satisfaction.

Further, the present invention is advantageous in that no skin preparation is necessary because the algorithm of the present invention is robust to skin conditions, as discussed below. This of course may help the clinicians to fit the prostheses more quickly.

System and Apparatus

Implementation of the method is explained by reference to one particular aspect of the present invention, namely a system where a computer is linked to a prosthetic device for calibration of the prosthetic device. In this regard, a standard computer, such as a personal computer, linked in any way to the device will suffice. For example, there could be a wireless connection or a standard USB connection between the computer and say the prosthetic device. Prosthetic devices are already calibrated in this way using a computer program loaded on a computer. MYOWIZARD™ and MYOASSISTANT™ software developed by VASI (901 Dillingham Road, Pickering, Ontario, Canada L1W 2Y5) and UTAH ARM 3™ developed by Motion Control, Inc. (115 North Wright Bros. Dr., Salt Lake City, Utah, USA 84116-2838) are examples of such computer programs that are designed to manually calibrate a one-degree-freedom prosthesis device (i.e. hand open/close). However, other systems and devices are contemplated and described below, and the method can be otherwise implemented, as described.

The present invention should also be understood as a means of calibrating a prosthetic device, and one or more prosthetic functions associated with the prosthetic device, to one or more discernible and reproducible muscle signals generated by a user. The system of the present invention, in another aspect thereof, comprises a prosthetic device, a computer linked to the prosthetic device, and computer programming loaded on the computer that enables the self-training functionality of the present invention. The computer program would include a calibration routine that enables our self-training method. In other words, the programming of existing computer programs could be modified to include this calibration routine, in a manner that is known. In addition, the computer program could be a standalone program that provides this functionality.

In one particular embodiment of the present invention, apparatus is provided comprising a prosthetic device incorporating the self-training functionality of the present invention. The functionality can be embedded by means of a microchip located within the prosthetic device in a manner that is known. The microchip could be embedded by hardwiring the functions on the microchip, or including control programming enabling the described functions, also in a manner that is known.

With respect to feedback, this particular embodiment could feature one or more push buttons to provide for user input. Pushing a button for a certain period of time could engage a calibration routine or training mode. Optionally, an indicator would show that the device is ready to be calibrated. A set period of time would be given to make the requisite movements. The next step would be to determine that the system is responsive. The device would then analyse the muscle signals as described. In a particular aspect of the invention, the device would then trigger the specific functions that the device based on its analysis has determined as being intended by the user. If the user determines that the device has been responsive, then the "mapping" would occur (in accordance with one implementation) by the device reproducing the functions in order, and in response the user attempting to trigger the applicable muscle signal. Retraining as described above could be initiated by engaging the push button again. This could be done to complete the calibration, as described before, or to initiate recalibration because of possible changes in applicable user generated muscle signals for reasons discussed earlier.

In another particular embodiment, the device could include a small display and programming to label particular functions, as described previously. The display could just simply be a few LEDs or an array of LEDs as indicators to provide feedback to the user. For instance, these indicators would display the current status of the system (i.e. training, mapping the functions, etc.). The display could be flat screens (i.e. coloured/monochrome LCDs) to provide more information about the status of the system graphically. These screens could be detachable to make the device lighter.

In another particular embodiment, the device could use a remote display, such as a computer monitor, or a TV screen. The connection from the device to the remote display could be done in any known means such as wireless RF link, infrared link, LASER link, ultra sound, USB, etc. Remote displays would be beneficial in applications that the cost and/or the heaviness are important.

The user would interact with the device as a means of pushing/touching a few buttons, a keypad, a touch screen, or any combination. It is also possible to embed a voice recognition system into the device to give the user the ability to interact with the device by just saying the desired commands.

It should be noted that in order to minimize the cost of such systems, the visual indicator could be replaced by audio feedback (i.e. constant beep, short beep, etc.). More expensive systems could take advantage of both audio and visual feedback.

In another aspect of an embodiment of the present invention, the apparatus comprises a controller for use in a prosthetic device, the controller incorporating a self-training routine in accordance with the present invention. In yet another aspect thereof, the apparatus of the present invention comprises a computer program that when loaded on a computer linked to a prosthetic device enables the prosthetic device to be calibrated based on a self-training routine in accordance with the present invention. In a still other aspect of the present invention, the apparatus of the present invention comprises a control program that is operable on a controller included in a prosthetic device, wherein the control program implements a self-training routine in accordance with the present invention.

Any devices embodying the present invention would include an instruction manual explaining how to "train" the device, further eliminating the requirement for professional assistance.

Visual Feedback

A visual display means is used to provide visual feedback to users illustrating the responsiveness of the system to muscle signals generated by the user, i.e. confirming that the particular device's functions correspond to the intended muscle signals. The use of a computer screen is one manner of providing visual feedback to the user. Other methods include LEDs, LED arrays, or small screen located on the device itself, as mentioned above. In powered prosthesis example, the visual feedback could be the hand functionalities (i.e. wrist rotation, finger movements, etc.) or any combination of above. It should be understood that the self-training aspect of the present invention also entails the customization of feedback by the user, as demonstrated in the Example below. In this regard, the invention enables calibration of devices in a way that the potential for language or comprehension playing a barrier is reduced.

Recording Sites

In a normal limb, at least two opposing muscles are required to control a joint. The interaction of agonist (a muscle responsible for producing a specific movement; this muscle contracts to move a limb) and antagonist (a muscle that relaxes while the agonist contracts) and often synergist muscles determines the action of the joint. Therefore, two-site control is a first step towards utilizing these natural interactions, which was chosen in this example.

Powered hand prostheses or systems controlled by muscle signals are usually controlled using two sets of electrodes, usually placed on the group of the flexor and the extensor muscles on the forearm.

It should be noted that the number of recording EMG sites can be increased without any limitations, but there is both a practical and theoretical limit to increasing the number of channels, with cost being an important factor.

Feature Extraction

The traditional goal of the feature extractor is to characterize an object to be recognized by measurements whose values are very similar for objects in the same category, and very different for objects in different categories. It is well known that the amount of force that a muscle generates correlates with the root-mean-square (RMS) value of the EMG signal of the corresponding contracting muscle. Therefore, RMS of the EMG signals could constitute the feature space. On the other hand, many researchers have used autoregressive (AR) coefficients as a possible feature space. In this example, the root-mean-square (RMS) value of each channel is calculated to create a 2-dimensional feature vector. The RMS values could be calculated as:

$$RMS(x_1, x_2, \ldots, x_n) = \sqrt{\frac{x_1^2 + x_2^2 + \cdots + x_n^2}{n}}, \quad (1)$$

Preferably, the response time for the control system should not introduce a delay perceivable by the user. This threshold is generally regarded to be roughly 300 milliseconds [References 10, 5]. This ensures that the algorithm makes decisions in less than 300 milliseconds. A 200-millisecond window is preferable in this example. It can be as small as 40 milliseconds (smaller windows than 40 milliseconds but the resolution may be less than desirable) in this example or make it unlimitedly large which is not desirable.

Figure 3A:
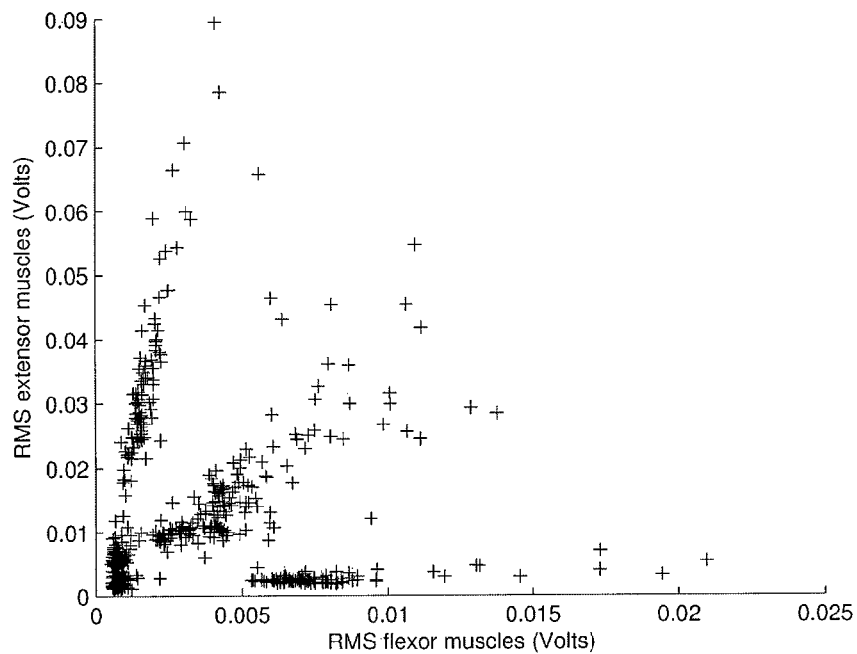
FIG. 3($a$) illustrates a plot of calculated RMS features from the extensor muscles versus the calculated RMS features from the flexor muscles for a 200-millisecond window.
Figure 3B:
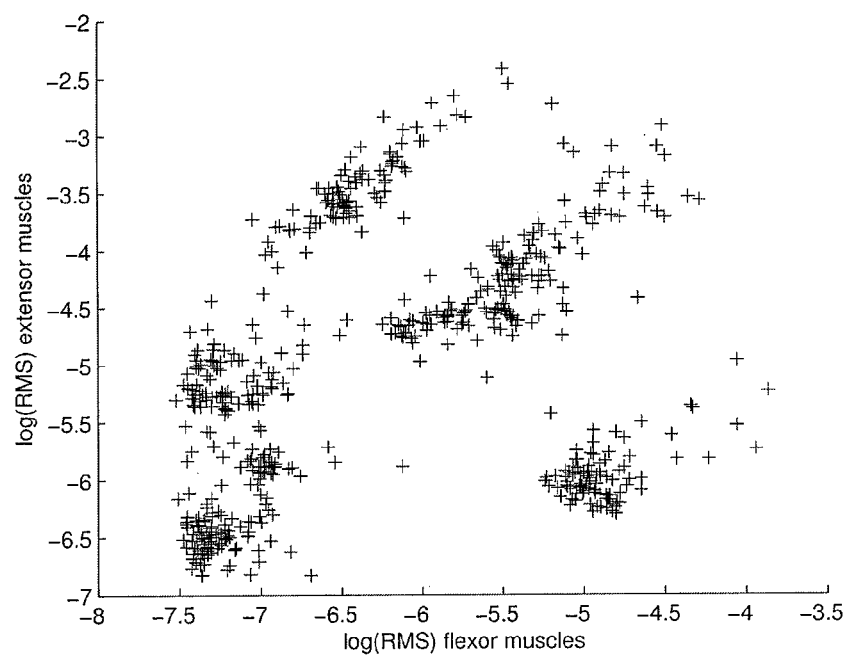

An example of calculated RMS features from the extensor muscles versus the calculated RMS features from the flexor muscles for each 200 millisecond window have been plotted in FIGS. 3(a) and 3(b) for an able-bodied subject. It is shown in FIG. 3(a) that data points are concentrated around the origin and they are spread across the axes. In order to spread the concentrated data points away from the origin and make the data points across the axes more clustered together, the natural logarithm of the RMS features can be calculated. RMS values of EMG signals are always positive. Therefore, the natural logarithm of the RMS features can be calculated and plotted, to form the feature space as follows:

$$F_{xj,yj} = (\log(RMS(x_{1j}, x_{2j}, \ldots, x_{nj})), \log(RMS(y_{1j}, y_{2j}, \ldots, y_{nj}))) \quad (2)$$

where $F_{xj,yj}$ is the calculated feature for the $j^{th}$ (j=1, 2, ..., N) feature. N is the length of the feature vector. $x_{1j}, x_{2j}, \ldots, x_{nj}$ are sample data points, recorded from flexor muscles (channel1), and $y_{1j}, y_{2j}, \ldots, y_{nj}$ are sample data points, recorded from extensor muscles (channel2). n is the length of the window over which the features were calculated. Assuming a 200 millisecond window and a sampling frequency set at 2000 samples per seconds, the length of the sequence would be n=400. Accordingly, it should be noted that simple feature sets can be calculated very fast even on an 8-bit microcontroller, and the delay time can be decreased from 200 milliseconds to any desired response time. FIG. 3(b) illustrates the effect of natural logarithm function on the feature space.

The raw data as well as the natural logarithm of RMS values of each channel can be recorded in a suitable format, e.g., MATLAB® format, for further analysis.

It should be understood that the feature extractor employed in the present invention is not limited to natural logarithm of root-mean-square values. The present invention contemplates different feature sets with this approach, such as $4^{th}$ order autoregressive coefficients and found that natural logarithm of root-mean-square still performs faster and better than other features.

Clustering

Clustering is one of the most important techniques in pattern recognition applications. In clustering, similar objects are grouped together. Each group is called a cluster. Different clusters are recognized by the dissimilarities among their members.

In one aspect of the current invention, fuzzy c-means clustering algorithm is applied to the feature set to find the different clusters of activities associated to different movements. At the end of the "training session", which will be explained below, each subject estimated the number of different performed movements. This number was taken as the number of clusters for the fuzzy c-means clustering algorithm. Fuzzy c-means is a data clustering technique wherein each data point may belong to multiple clusters with varying degrees of membership. It is based on minimization of the following objective function:

$$J_m = \sum_{i=1}^{C} \sum_{j=1}^{N} (\mu_{ij})^m \|x_j - c_i\|^2. \quad 1 \le m \le \infty \quad (3)$$

where m is the fuzziness index, $\mu_{ij}$ is the degree of membership of observation $x_j$ in the cluster i, $x_j$ (j=1 ... N) is the $j^{th}$ d-dimensional data point, $c_i$ is the d-dimensional center of the cluster, and $\|.\|$ is any norm measuring the similarity between an empirical data point and a cluster center [Reference 20]. Reference 21 showed the best choice for m is probably in the interval [1.5, 2.5], whose mean and midpoint, m=2, have often been the preferred choice for many users of fuzzy c-means.

Fuzzy partitioning is carried out through an iterative optimization of the objective function (1), with the update of membership $\mu_{ij}$ and the cluster centers $c_i$ by: [Reference 20]

$$\mu_{ij} = \frac{\left[\frac{1}{\|x_j - c_i\|^2}\right]^{\frac{1}{m-1}}}{\sum_{i=1}^{C} \left[\frac{1}{\|x_j - c_i\|^2}\right]^{\frac{1}{m-1}}} \quad (4)$$

$$c_i = \frac{\sum_{j=1}^{N} (\mu_{ij})^m x_j}{\sum_{j=1}^{N} (\mu_{ij})^m} \quad (5)$$

Figure 4A:
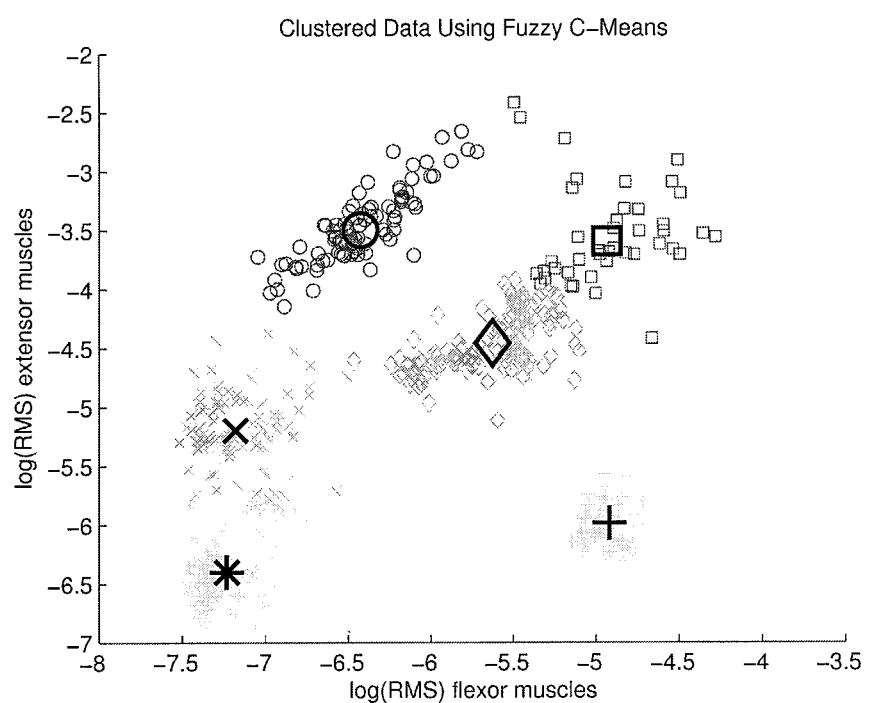
FIG. 4($a$) illustrates an example of clustered data for six movements associated with six different clusters.

The generated clusters along with the centers of the clusters can be shown on a computer screen. FIG. 4(a) shows an example of the clustered feature space.

Although the number of clusters can be set by the user, it can be automatically found by some other methods such as cluster validity algorithms. Examples of these algorithms are but not limited to Partition Coefficient (PC), Classification Entropy (CE), Partition Index (SC), Xie-Beni separation index, Silhouette Validation Method, etc. These algorithms mathematically justify the optimum number of clusters. There are also other clustering algorithms available that return the correct number of clusters automatically to be passed to fuzzy c-means algorithm. Subtractive Clustering is an example of this type of clustering methods. However, these types of clustering require some other manual fine-tuning and tweaking processes, which are not desirable for the present invention. For instance, in subtractive clustering the following parameters should be supplied to the algorithm:

The radius of clusters: Small cluster radius values generally result in finding a few large clusters.

Quash factor: This is the factor used to determine the neighbourhood of a cluster center, so as to quash the potential for outlying points to be considered as part of that cluster.

Accept ratio: This sets the potential above which another data point will be accepted as a cluster center.

Reject Ratio: This sets the potential below which a data point will be rejected as a cluster center.

Further, it should be understood that the algorithm employed in the present invention is not limited to fuzzy c-means clustering. As mentioned above, some other fuzzy clustering algorithms such subtractive clustering, as well as none-fuzzy clustering such as k-means algorithm can be used. The choice of the clustering algorithm may affect the performance of the system.

Classification

For classifying new data after a training session, the fuzzy membership values based on Equation (2) were calculated for each new point and in turn, each point was assigned to the cluster to which it had the highest membership. Consequently, the new points were classified in real-time. In order to make a user-friendlier environment for the user to interact, visual feedback is provided to the user.

Figure 4B:
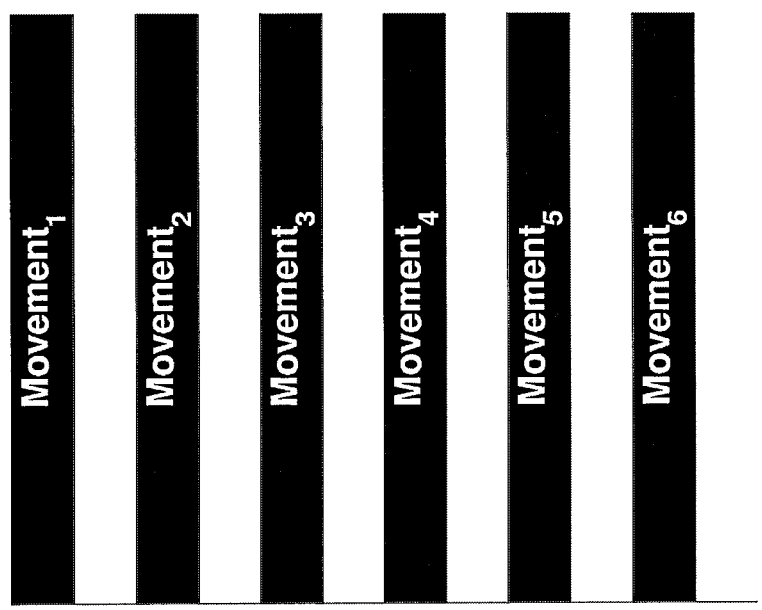
Figure 4C:
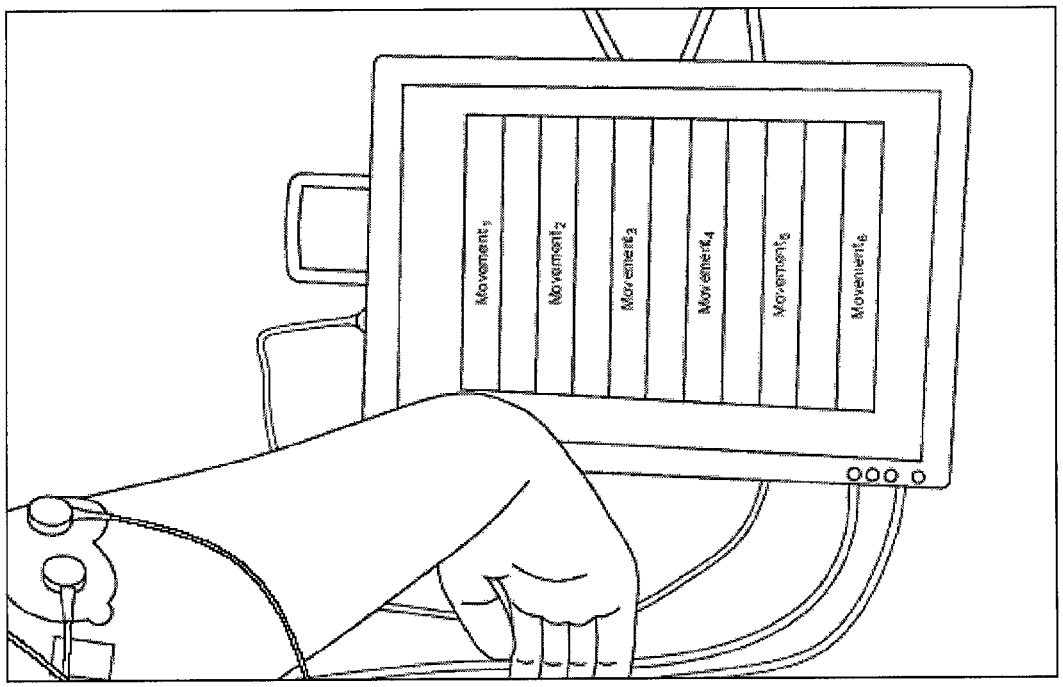

In a particular embodiment of the present invention, a computer program displays a window consisted of separated vertical blue bars. Each bar is associated with a specific cluster. The bars are labelled arbitrarily as Movement 1 to Movement n, where n was the $n^{th}$ cluster. FIGS. 4(a), 4(b) and 4(c) show a complete example of the clustered data and the user interface for six movements associated with six different clusters (forearm movements). For each new data point, the software program highlights the corresponding vertical bar in red, as soon as the maximum membership value of the new point was discovered.

Figure 7A:
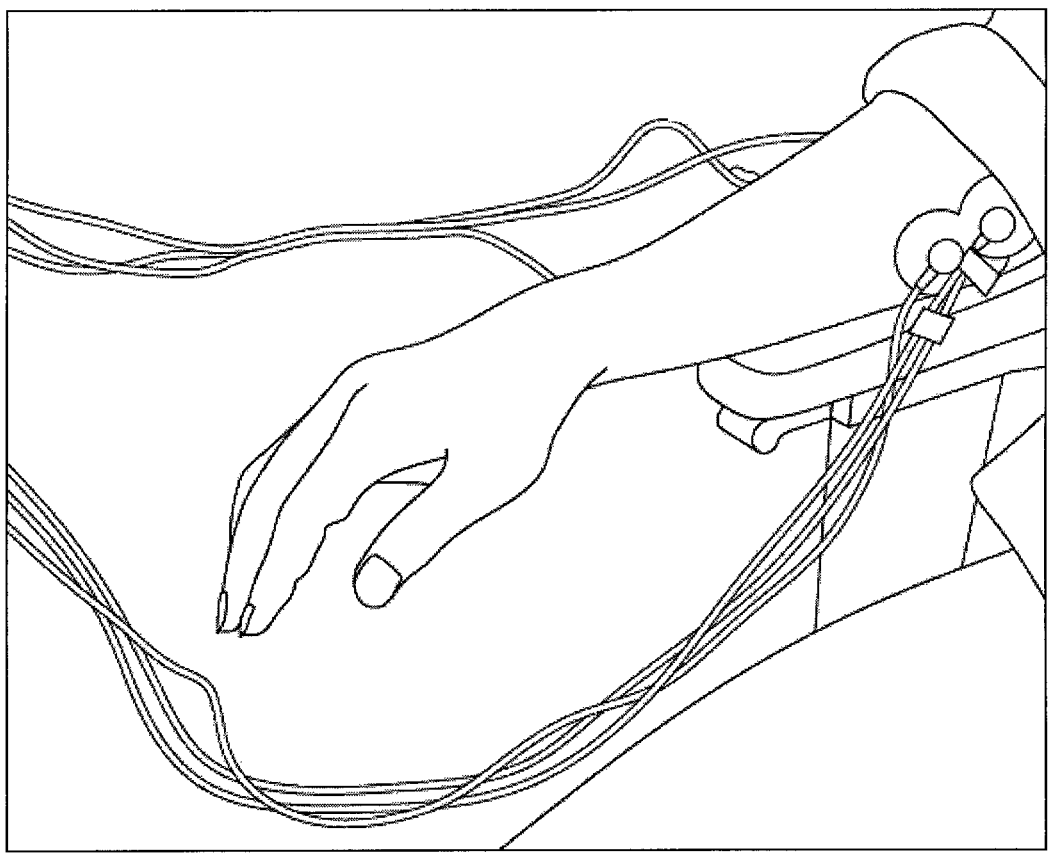
FIGS. 7(*a*) thru 7(*f*) illustrate an example of a user performing six different forearm movements.
Figure 7B:
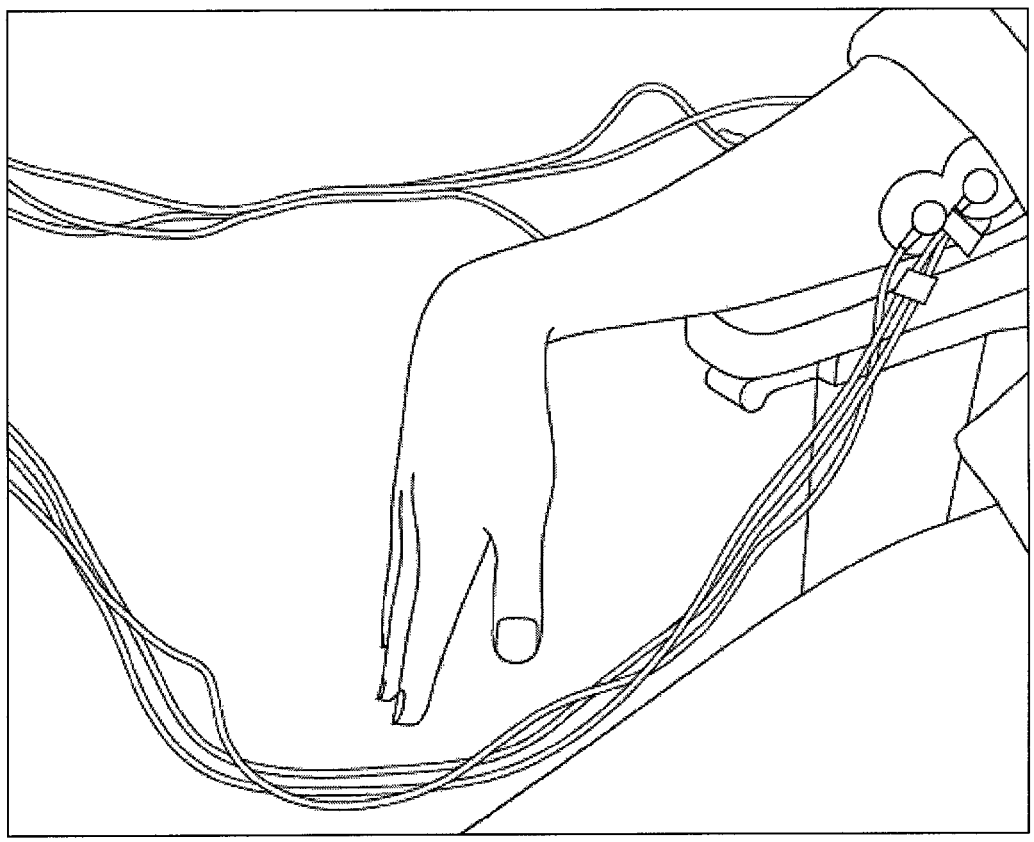
Figure 7C:
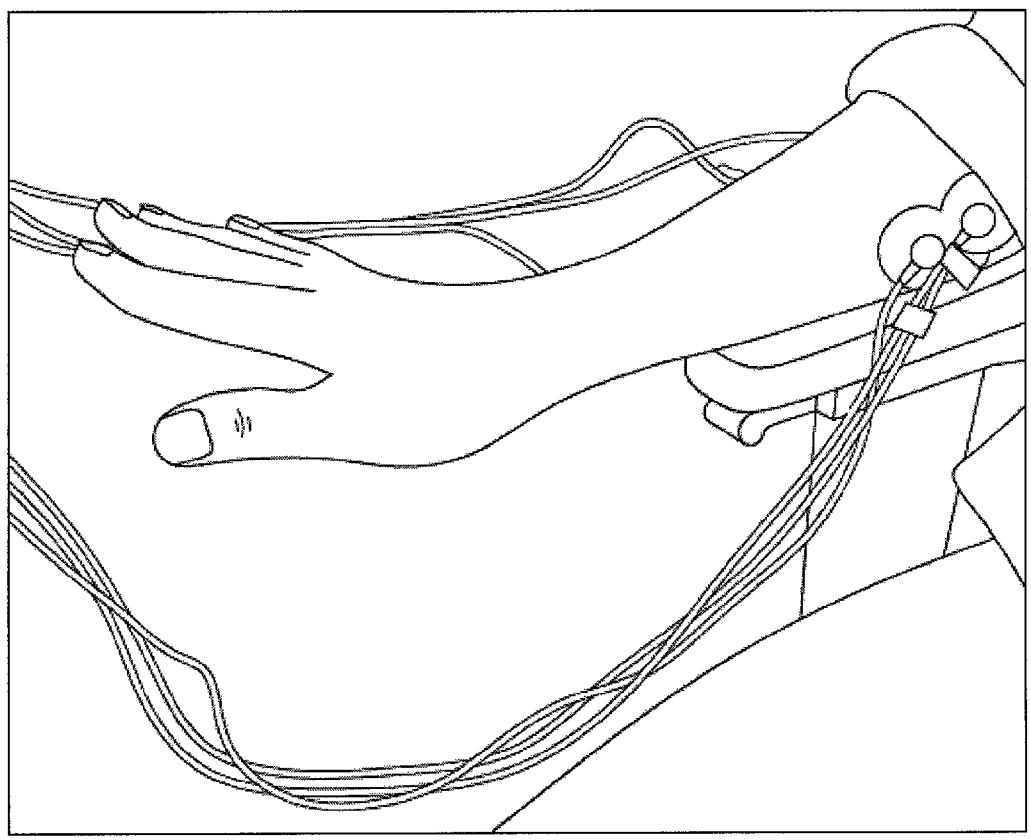
Figure 7D:
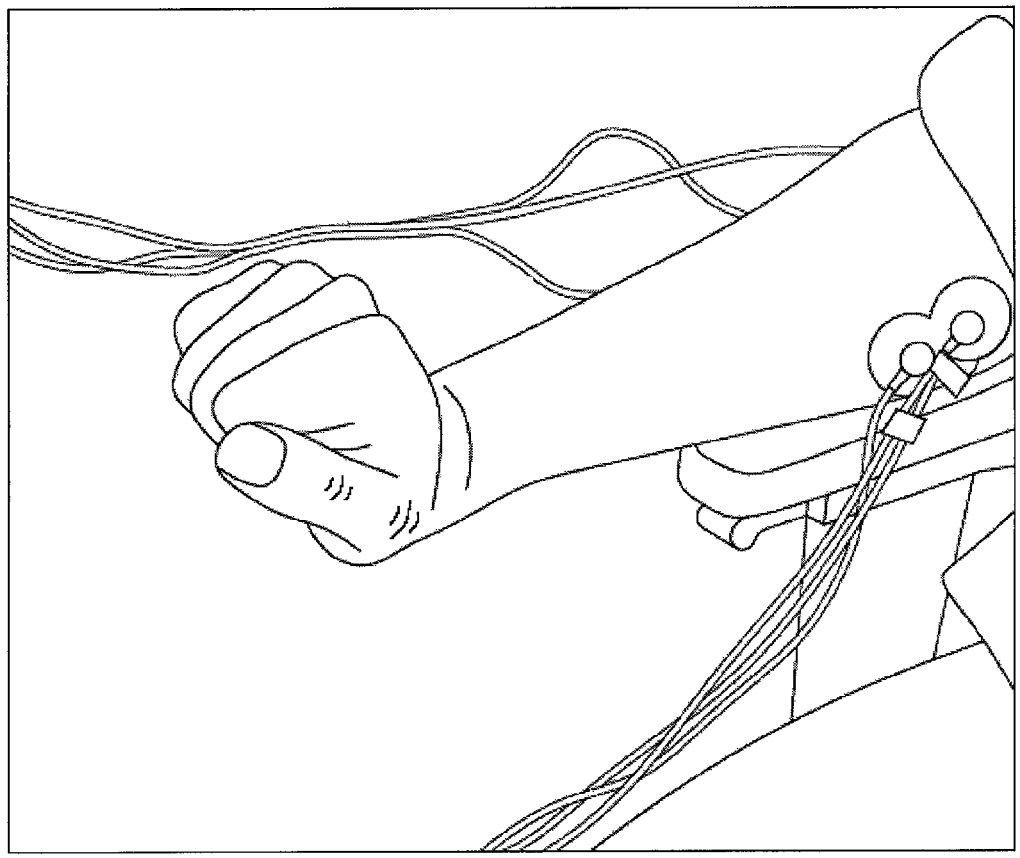
Figure 7E:
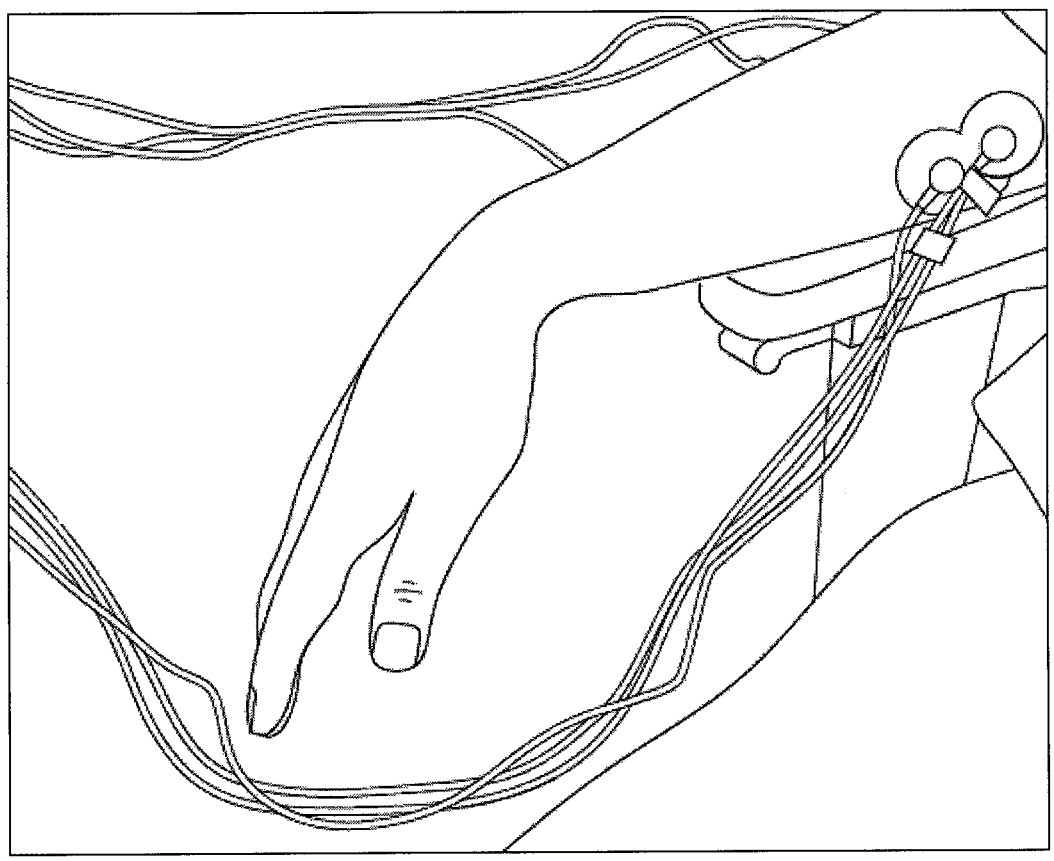
Figure 7F:
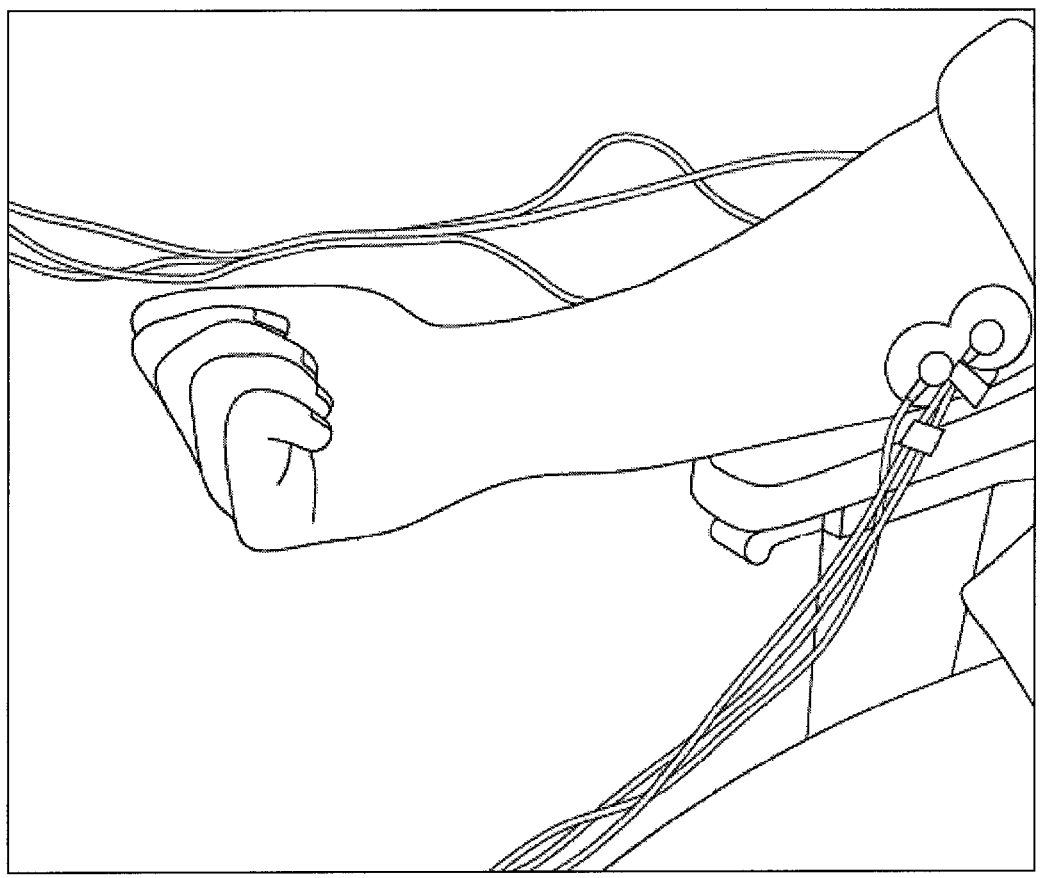

FIG. 4(b) depicts an example of visual feedback, and FIG. 4(c) shows an example of a user who is using the visual feedback as a response to his forearm movements. Examples of a user performing six different forearm movements are depicted in FIGS. 7(a) thru 7(b). In this example, the user is doing wrist flexion and the computer responses to the user by highlighting the first bar from the left on the computer screen. The visual feedback may be different from one application to another. For example, in a prosthetic application, the visual feedback can be designed as a simulated multi function prosthetic hand. This would help the user to interact with the system more naturally.

Applications

This algorithm can be used to map two or more recording EMG sites to any desirable functions, based on the ability of the user. Therefore, in addition to multifunction power prostheses, the present invention encompasses gaming applications, and could enable control of writing apparatus, or any input device to a computer, e.g. a modified mouse. In a further aspect of the present invention, a gaming apparatus is provided, wherein the gaming apparatus includes the self-training functionality of the present invention for mapping muscle signals to one or more gaming functions of the gaming apparatus. The algorithm aspect of the present invention can be simply used as a user interface for any device that requires a few user inputs to be mapped into different functions. Special keyboards/mice for computers, game pads, environmental control devices (garage door openers, light switches, etc.), electronic musical instruments, etc., are all examples of such devices. The present invention could be embedded into a system that could be a link among the user's muscle signals and the inputs of the aforementioned standard control systems.

For example in a commercially available standard game pad, the user would like to control an animated character in the game to go up, down, turn left, right or jump by pressing corresponding buttons on the game pad. A device that is powered by the proposed invention, could completely replace such control systems. For example, in game pad scenario, such a device could be designed based on this algorithm to take the user's self-selected commands from the user's muscle signals on the user's forearm (i.e. 5 or 6 commands on each forearm, total 10-12 commands) and associates each distinct forearm movement to each unique function of the gaming device. For example, the user's flexion on the forearm could make the character go up and making a fist on the user's right hand could make the character to jump. In this example, the device may include 2 input channels to record the user's muscle signals. The device will include embedded amplifiers, filters and analog to digital converter to make the signals meaningful for the embedded processing unit. This unit may take the user's command by any known means (i.e., push button, keypad, voice-activated switches) and provide the visual feedback to the user in the manner that is known (LEDs, LCDs, 3-dimensional LASER displays, remote displays, TV screen, etc.). Configuring and calibrating such a device to serve as control system can be done in the following easy three main steps:

1. The user would instruct the device to go into 'Training mode' and the device would acknowledge the command by providing the predefined feedback.
2. When the user trains the system in a timely manner, it asks the device to estimate different repeatable movements. As mentioned earlier, the number of different movements (clusters of features associated to each movement) could be manually or automatically passed to the clustering algorithm. When the algorithm clusters the feature space to estimate different movements, it prompts the user to test the system responsiveness. As mentioned above, in one example of implementation, the user tries to perform different movements randomly and the device would show a visual/audio signal, which was randomly associated to each distinct movement by the device after the clustering. If the user finds the system non-responsive, it may retrain the system again.
3. When the user feels that each performed movement creates a distinct audio/visual feedback by the device, the system is considered responsive and it will ask the device to go into 'mapping mode.' In accordance with one implementation, the device reproduces the preset functions, which were required by the application (i.e. up/down/left, right, jump) in order, and in response, the user attempting to trigger the applicable muscle signal. The user may confirm the selection by giving the input to the system in any known manner that was mentioned earlier. When the 'mapping' finishes, the system is calibrated and ready to use. Now in this example, the user is capable of controlling an animated character on a standard gaming device just by initiating different muscle signals, associated with different movements, with which the user trained the system.

In another example, it is also possible to use such devices as a link between the user's muscle signals and the current commercially available game pads, and let the standard game pad control the gaming device. In this scenario, each muscle signal is linked directly to each desired button on the standard game pad (serve as an input to the game pad not the gaming device itself), and it is not replacing the game pad in a gaming device, entirely.

It can easily be seen that other similar control applications such as special keyboard, a mouse for computer, electronic musical instrument, environmental control systems, share more or less the same configuration, including the main three steps of 'training', 'testing the responsiveness' and 'mapping', described earlier.

The algorithm aspect of the present invention can also be simply used to control the powered prosthetic hands currently available, which can only open and close, such as those manufactured by VASI, Otto Bock Healthcare and Motion Control, Inc., among others. The additional functions can be mapped to give the prosthesis more functionality. For example, tight fist and soft fist movement (Subject7 in the following example), can control the rate of the opening or closing the powered prosthetic hand.

Different membership values within a specific cluster can also be mapped to control the rate of a specific movement. For example, the data points closer to the center of the cluster can introduce higher speed in performing a specific movement.

There is also a possibility to introduce a 'neutral' class by setting a threshold for the membership values of the data points within clusters. This can eliminate the sensitivity of the algorithm for the data points that may appear right on the boundary of adjacent clusters.

EXAMPLE 1

A. Participants

In a study, 8 able-bodied adults and 1 below-elbow amputee were recruited. Able-bodied subjects consisted of a convenience sample of adults aged 20-30 years with no upper limb deficiencies. An amputee was recruited from a local rehabilitation center. It was particularly desirable to choose an amputee who was not a powered prosthesis user since he or she would most likely be unfamiliar with forearm muscle control. This lack of prior training would present a nontrivial challenge to the automatic separation of EMG signals.

B. Data Acquisition

Figure 5A:
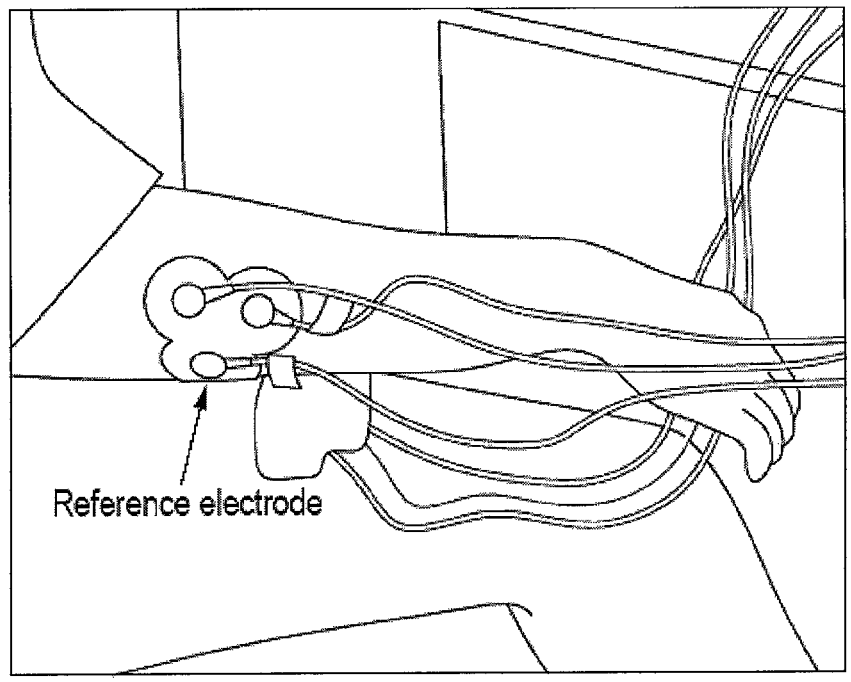
FIGS. 5(*a*) and 5(*b*) illustrate the placement of reference electrodes on the bulk of a user's forearm muscles.
Figure 5B:
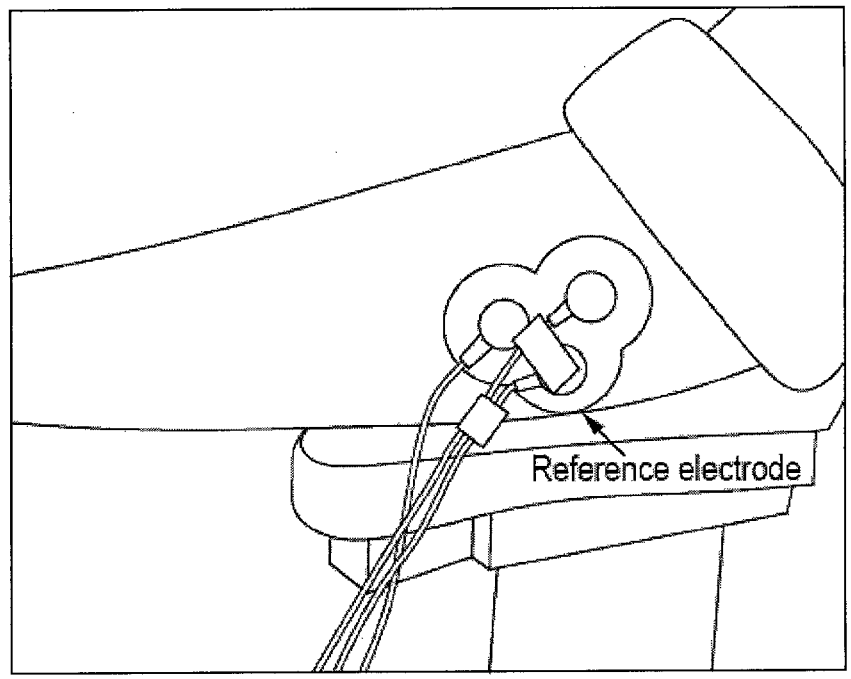

The raw EMG signals were recorded from two sites on the forearm, using pregelled Ag/AgCl GRASS F-E8SD disposable electrodes. The electrodes were placed in pairs with one reference electrode at each site, as discussed below. As the robustness of the algorithm to any skin conditions was to be investigated, no skin preparation was needed. It has been reported that the bulk of the muscle produces higher amount of EMG signals so that it was desirable to put the electrodes on the bulk of the muscles [Reference 22], as illustrated in FIGS. 5(a) and 5(b). The location of the attached electrodes on the forearm was photographed for the future reference. The signals were amplified by a GRASS TELEFACTOR 15A54 amplifier. This amplifier conforms to the Underwriters Laboratories (UL) 2601-1 safety standard and certified to Canadian Standard Associations (CSA) C22.2#601-1 safety standards. In this study, the gain of the amplifier was set at 5000 and the signals were band-passed inside the amplifier. Although many studies have suggested the usable band for EMG signals is from 20 Hz to 500 Hz [References 23, 22], due to the setting limitations on the amplifier, the chosen band for this experiment was set at 30 Hz to 1000 Hz. The low cut-off frequency filter was used to avoid motion artefact [Reference 22]. Built-in line 60 Hz notch filter was used in addition to the primary filters to eliminate the power line 60 Hz noise. The amplified signals then were fed to a personal computer (P4-2.8 GHz, 1 GB RAM) equipped with a National Instrument, 16 bit data acquisition board, PCI-6014. The signals were sampled at 2000 samples per seconds to avoid aliasing. The necessary software program responsible for initializing the data acquisition board and recording the data was written in MATLAB® 7.1.

As stated above, in the end user application, the electrodes, data acquisition system, amplifier and filters can be embedded into any hardware to minimize the space and increase the portability of the system. The firmware/software can be implemented in any intelligent semiconductors such as microcontrollers/FPGAs or DSP chips as desired in a manner that is known.

C. Training

The experimental protocol utilized in the study is summarized in FIG. 1. The algorithm simply extracted the features from the raw EMG signals recorded at two sites, and clustered the feature space. The membership value for each data point was calculated and used for classification. A testing session at the end, estimated the performance of the algorithm. This section is not required for end user applications. It was done here to estimate the reliability of the system.

As mentioned previously, the objective is to automatically define different self-selected intentional movements. Therefore, the subjects were not restricted to any predefined sitting position. However, in order to establish a well-defined and repeatable resting position for each individual, each subject was asked to sit on a chair, to relax and to rest his or her arm in the most comfortable position. There was no visual feedback provided. Instead, the subjects were asked to concentrate on their forearm movements and try to produce as many as different forearm movement they could naturally and repeatedly create, as soon as the computer prompted.

Figure 6:
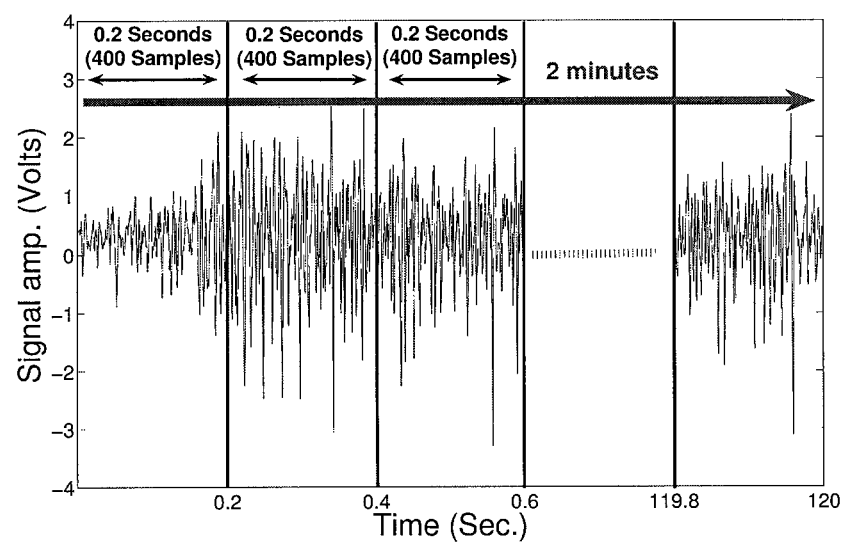
FIG. 6 illustrates an example of the data extracted in a 200 millisecond window in real-time.

The lack of visual feedback could help the computer learn more naturally from the subject's self-selected intentional movements. The computer started to extract the features every 200 millisecond window in real-time, as illustrated in FIG. 6. All necessary data were saved in both the computer memory and the hard drive. This session was considered a "training session" and it ended after recording of two minutes worth of data. The subject could rest at any time while the data were being recorded.

D. Clustering

At the end of the training session, fuzzy c-means clustering algorithm was applied to the proposed feature spaces, to find the different clusters of activities associated to different movements. Each subject estimated the number of different performed movements. This number was taken as the number of clusters and applied to the fuzzy c-means clustering algorithm. The generated clusters along with the centers of the clusters were shown to the user on the computer screen. FIG. 4(a) illustrates an example of a clustered feature space using fuzzy c-means algorithm.

As stated earlier, the number of clusters can be estimated automatically by employing some other clustering algorithms such as subtractive clustering and/or cluster validity algorithms such as Silhouette validity index.

E. Membership Values for Classification

For classifying new data after clustering the feature space formed by the training session, the fuzzy membership values based on Equation (4) were calculated for each new point and in turn, each point was assigned to the cluster to which it had the highest membership. This process in this example repeats every 0.2 seconds. Therefore, for every 0.2 seconds, we have a classified feature in real-time.

F. Labelling the Clusters

The visual feedback consisted of vertical blue bars provided to the subject. These bars could be highlighted by the user's forearm movements. At the end of the training session, the user was given a chance to highlight the bars by performing the same forearm movements performed during training for another two minutes, to find the relationship among the movements and the highlighted bars. At the end of this session, if the user felt that the system responded to his movements accordingly, the software would ask the subject to label the movements. Otherwise the system would ask the subject to retrain the system. This could happen due to two main reasons:

1. The subject did not train the system properly and did not provide repeatable natural movement during the training session.
2. The fuzzy c-means algorithm converged to a local minimum so that the points are not assigned properly to the clusters. A cluster validity algorithm may help overcome this problem by validating the created clusters and suggesting reclustering the feature space, to find clusters that are more appropriate.

The subjects were asked to label the vertical bars, which corresponded to their forearm movements. They could label the movements in any language or with any words, which would help them to remember the movement. In the order to estimate the performance of the system, this step was necessary. As it will be discussed in testing session for estimating the accuracy, the computer needed to ask the user to perform one of the movements randomly. Therefore, labelling the movements was necessary.

Figure 8A:
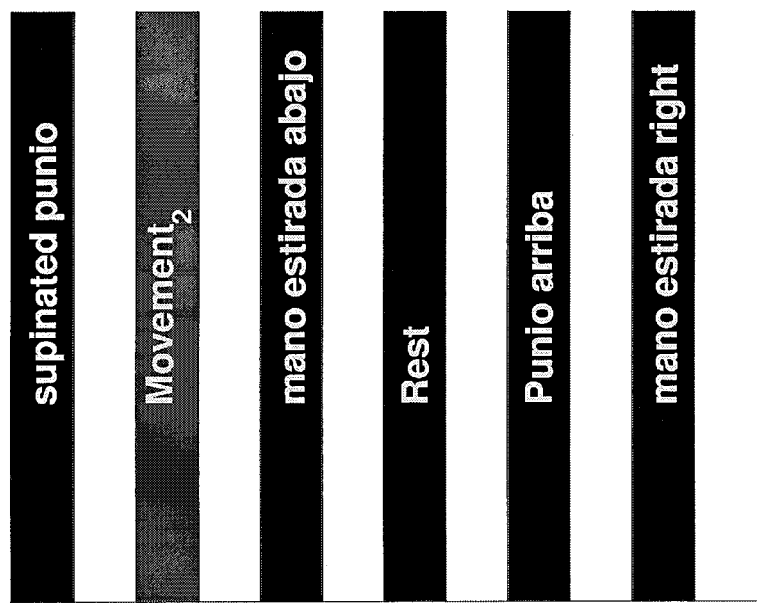
FIGS. 8(*a*) and 8(*b*) illustrate an example of the visual feedback in accordance with six different movements and the resulting clustered data.
Figure 8B:
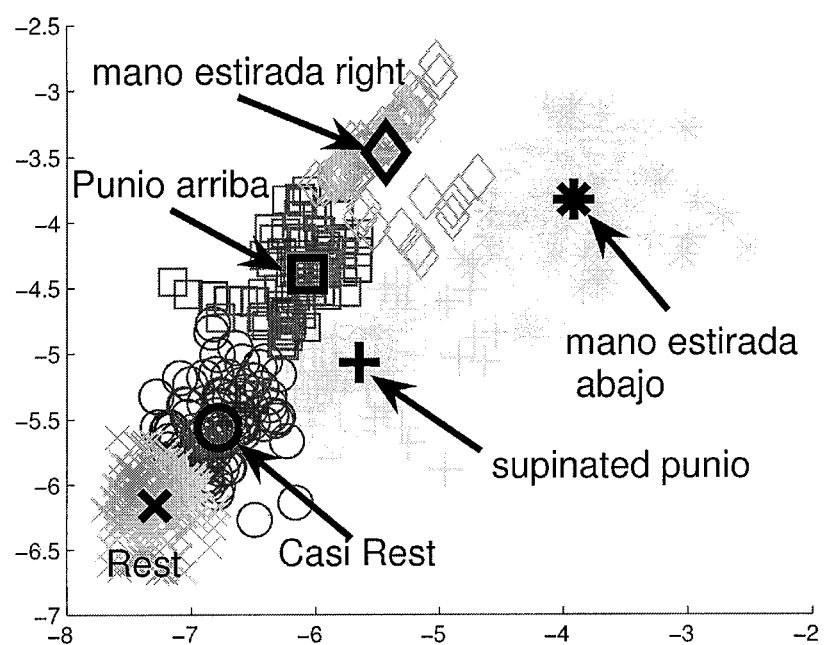

For each movement, the user was given five seconds to choose any of the unlabelled bars (movements) to label. An example of six different movements and their corresponding labelled vertical bars are illustrated in FIGS. 8(a) and 8(b). In this example, the subject used English-Spanish words to label the movements. The subject expressed that those chosen labels were meaningful to him and could help him remember how he created those movements.

G. System Responsiveness

When the discovered movements were labelled, the subjects were given another one minute to get accustomed to the labelled movements. They were asked to choose any of the movements randomly and try to highlight the corresponding vertical bars by performing the same forearm activities with which they trained the system at the training session.

H. Testing

In order to estimate the error, the user was required to perform one of the labelled movements randomly. Therefore, a random sequence representing the movements' indices had to be generated. A uniform random sequence of length of N, consisted of indices representing movements, was generated. The length of the sequence was 10 times as long as the number of generated movements. This would assure that each movement was asked randomly 10 times during the testing procedure.

I. Results

To estimate the error, a movement was considered as an intentional self-selected movement when the subject could maintain the contraction for five consecutive 200 milliseconds sampling windows. This assured algorithm that the subject did not pick the movement by chance and in fact, it was the intended movement by the subject. Each sampling window was a 200-millisecond window when the features were calculated. The performance was calculated by:

$$R_i = \frac{M_i}{k}, \quad i = 1 \ldots n \qquad (6)$$

where $R_i$ was the calculated performance for $i^{th}$ movement, $M_i$ was the number of correct movements for $i^{th}$ movement, n was the total number of different movements and k was the number of repetition for each requested movement by the computer. This number was set at 10 in this study. The subject accuracy was simply calculated by averaging all movement performances.

The examples of a subject's performance results and the lone amputee's performance results (Subject9) are shown in Table 1 and Table 2, respectively. Name of the movement is the label that the subject chose, based on his or her own perception of the movement. Cluster index is an index number, which the computer internally uses to refer to each movement. The subjects trained the system based on their self-selected intentional movements. As a result, the number of movements, the way the movements were created and the labels were different among these subjects. In this example, it can be seen that the able-bodied subject created six different movements with 96.67±4.71 accuracy while the amputee subject, who never used a powered prosthetic hand before, created 4 movements with 87.50±12.99 accuracy.

TABLE 1

Performance results from Subject7.

| Name of the movement | Cluster index | Accuracy (%) |
| --- | --- | --- |
| Palm | 2 | 100.00 |
| Rest | 4 | 100.00 |
| Soft Fist | 1 | 100.00 |
| Tight Fist | 3 | 100.00 |
| Down | 5 | 90.00 |
| Fist UP | 6 | 90.00 |
| Subject performance | N/A | 96.67 ± 4.71 |

TABLE 2

Performance results from Subject9 (amputee).

| Name of the movement | Cluster index | Accuracy (%) |
| --- | --- | --- |
| Wrist right | 3 | 50.00 |
| Wrist down | 2 | 100.00 |
| Twist right | 4 | 70.00 |
| Rest | 1 | 100.00 |
| Subject performance | N/A | 87.50 ± 12.99 |

Table 3 illustrates the results obtained from all the participants in this example. As mentioned earlier, Subject9 was the only amputee who participated in this study and never used a powered prosthesis before.

TABLE 3

| | Experimental Results. | | | |
|---|---|---|---|---|
| Subject | Accuracy (Mean among movements (%)) | No. of user-specified movements | No. of performed movements ≧80% | Accuracy for movements ≧80% (%) |
| Subject1 | 75.00 ± 18.93 | 6 | 3 | 90.00 ± 8.16 |
| Subject3[2] | 90.00 ± 12.65 | 5 | 4 | 95.00 ± 8.66 |
| Subject4 | 94.00 ± 4.90 | 5 | 5 | 94.00 ± 4.90 |
| Subject5 | 85.00 ± 17.08 | 6 | 5 | 92.00 ± 7.48 |
| Subject6 | 48.89 ± 39.85 | 9 | 4 | 92.50 ± 4.33 |
| Subject7 | 96.67 ± 4.71 | 6 | 6 | 96.67 ± 4.71 |
| Subject8 | 86.00 ± 8.00 | 5 | 5 | 86.00 ± 8.00 |
| Subject9[3] | 56.00 ± 37.20 | 5 | 2 | 95.00 ± 5.00 |
| Subject9[3] | 87.50 ± 12.99 | 4 | 3 | 93.33 ± 9.43 |
| Group Average | 79.90 ± 16.81 | 5.67 ± 1.41 | 4.11 ± 1.27 | 92.72 ± 3.18 |

J. Dynamic Adaptation

Most of the previous works that used other approaches such as ANN or genetic programming were not adaptive over time: once the network is trained, it is very difficult to retrain the network in real-time based on the newly recorded EMG data. It was shown in previous studies that a subject's ability to produce the same EMG data over time varies [Reference 4]. In contrast, our approach may overcome this problem in real-time applications as it keeps finding new clusters based on both the previous and new data. It uses very small amount of data points (600 points for a 2 minute training scenario). As our proposed algorithm keeps a record of the previous data, it was expected that it would find new clusters based on the dynamic change in the EMG signal. This means that the algorithm is robust to this change and more importantly, is not user-dependent. In other words, in order to make the system dynamically adaptive over time, the system should keep track of the history of the features in the memory and recluster the feature space from time to time. This helps the algorithm to find the change in the old clusters and redefine new clusters based on the possible change in the feature space. Therefore, the dynamic adaptation is realized by the slow transition from the older clusters to the newly defined clusters.

K. Majority Vote

In the experimental test, in order to make the system more robust, the algorithm waited for five consecutive movements (one second) before assigning the performed movements into any of the obtained categories. It is possible to decrease this delay by the total of 200 milliseconds. (5 consecutive movement×40-millisecond window to process EMG=200 milliseconds.) This type of majority vote scheme appears to increase the robustness of the system [Reference 27].

L. The Learning Curve

It should be noted that all the participants in this study encounter this system for the first time and they trained the system only once, for 2 minutes. As all human beings have a learning curve to learn how to use a system, it is expected that the accuracy of the system increase and the required training time decrease by performing more trials. The surprisingly high accuracy for the lone amputee participant in this study (Subject9-Trial2) shows that the system can be trained by the amputees based on their own self-selected intentional movements. These movements are natural to the amputees, which may not be natural or even typical to able-bodied individuals. (Note the labels chosen by the amputee in Table 2). The amputee participant expressed extreme satisfaction by the system responsiveness. The training does not impose any restriction on the subject and the system learns from the subject's self-selected intentional movements naturally.

M. Noise Analysis

Common noise (Electrical noise, motion artefact, unprepared skin conditions, etc.) has been embedded in the clusters. In order to clarify this, consider the 'Rest' movement. If there were no noised in the system, all points in 'Rest' region in the feature space would be mapped into one point. However, as it was mentioned earlier, the 'Rest' region as well as other regions, constituted a cluster. This variation in the clusters showed the system noise. Therefore, the system is somewhat robust to noise, as noise has been embedded in to the clusters. The robustness of the system is proportional to the power of the noise: the higher the noise level, the higher variance in the cluster regions. The system would be robust to noise as long as the variance in the noise does not make the clusters overlap.

N. Steady State EMG Signals vs. Transient EMG

Unlike previous studies that tried to classify the EMG signal both/either by examining the steady state signal and/or transient signal, the present invention captures both data into one cluster automatically. Unlike the prior art, there is no need to introduce both a threshold and a delay into the system to separate steady state EMG from transient EMG. Therefore, the system is more reliable and has a faster response time.

MMG Implementations and Example

MMG signals can be implemented in the present invention the same way as EMG signals. However, MMG signals usually have much lower bandwidth than that of EMG. The majority of MMG signals are seen within 0 to 50 Hz bandwidth. Therefore, these signals should be filtered beyond 50 Hz (in some cases beyond 100 Hz) and any sampling rates twice the bandwidth or higher can be used to digitize the signal. In this investigation, as we required the minimum setup change on our hardware, the sample rate was set at 1000 Hz and 200-millisecond window was chosen to calculate the features. It should be noted that based on the requirement, the length of the sampling window can be changed as well as the sampling frequency.

As discussed earlier, there is no limitation in the number of input channels. The only difference is the choice of the feature sets. Several feature sets were investigated and it was found that the standard deviation among 5th order autoregressive coefficients (AR) demonstrated great results.

Figure 10:
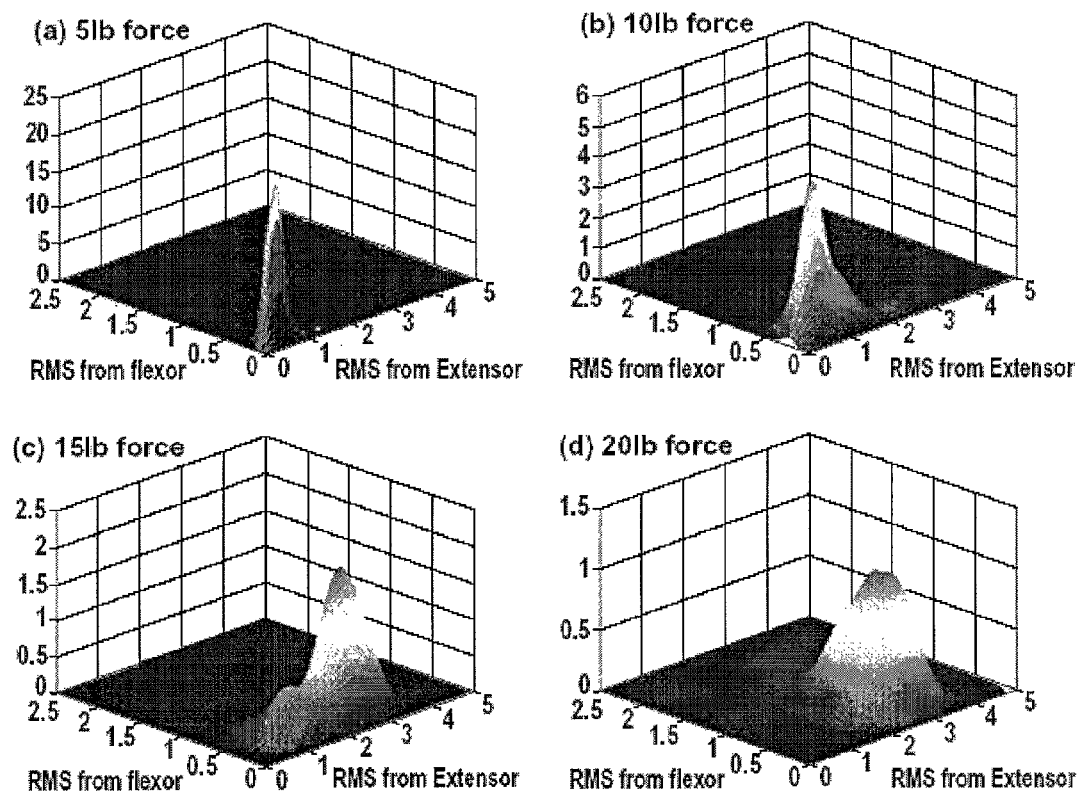
FIG. 10 illustrates the application of the system for monitoring changes in muscle activity by using different fuzzy membership functions for forearm MMG as a result of different loading conditions.

MMG implementations of the present invention that would include the following:

Automatic fatigue detection/monitoring: The system of the present invention is operable to detect/monitor changes in muscle signals. For example, for workers who are constantly lifting heavy objects, the system could be used to automatically detect muscle fatigue and heightened risk of injury. For athletes or individuals interested in exercise science, the present invention could be used to non-invasively monitor when muscles have been maximally exerted. We can use simple rules to flag a change and update the fuzzy partition functions or re-estimate the cluster centers. These changes are manifested as alterations in the characteristics of the clusters arising from fuzzy clustering. In particular, the location and the shape of the cluster may change. Fatigue is one instance in which muscle signals are known to change. Another example is loading of the muscle with different amounts of weights. We have demonstrated that with the proposed system we can track such changes as they occur. FIG. 10 shows different fuzzy membership functions for forearm MMG as a result of different loading conditions. Clearly as loading increases, the cluster moves and changes shape, as reflected in the changing fuzzy membership function.

- Programming by demonstration: This is a technique used to train robotic manipulators using motions of the natural human hand. The invention could be used to characterize the muscle activity of the natural human hand. That information could in turn be used to drive actuators of the robotic limb to perform coordinated, life-like motion.

- Hybrid prosthetic control systems: The present invention could be used to create hybrid prostheses which combined EMG and MMG control signals, reaping the benefits of both phenomena to enhance classification accuracy and robustness to changing physiological and environmental conditions.

- Gaming interface: As mentioned before in describing EMG-only applications. The present invention could also have EMG-MMG hybrid interfaces.

- Access channel: For individuals who have quadriplegia with some residual motor activity (e.g., slight muscle twitches), an MMG implementation of the present invention could provide a channel of access to communication, environmental control or any switch-enabled technology. For example, the clusters could represent different navigational commands or messages.

- Wheelchair control: The combination of EMG and MMG could also be used to drive a wheelchair. Different clusters could represent different navigational commands (e.g., go forward, stop, turn). EMG alone would not be reliable enough.

Autoregressive (AR) Coefficients Feature Space

The AR model of the current sample of the signal x(j) is described as a linear combination of previous samples plus an error term e(j) which is independent of past samples:

$$x(j) = -\sum_{k=1}^{p} a_k x(j-k) + e(j). \quad j = 0, 1, \ldots, n-1. \tag{7}$$

where x(j) are the samples of the modeled signal, $a_k$ are the AR coefficients, p is the model's order, e(j) is the time series of residual values (prediction errors), and n is the length of the window over which the features were calculated. The model can be interpreted as a linear system with e(j) as its input (white noise) and x(j) as its output. The transfer function H(z) for the AR process is:

$$H(z) = \frac{X(z)}{E(z)} = \frac{1}{1 + \sum_{k=1}^{P} a_k z^{-k}} \tag{8}$$

The spectrum of the model can be estimated from Equation (8) as:

$$P_{AR} = \frac{1}{\left|1 + \sum_{k=1}^{p} a_k e^{-j\omega k}\right|^2} \tag{9}$$

There are many ways to compute AR coefficients. The Burg algorithm [Reference 29] is probably the most widely known AR procedure. In this study, the 5th order AR coefficients on each recording site were calculated to form a 10-dimensional feature space. Unfortunately, the higher the dimension of the feature space, the more the number of samples required for AR coefficient estimation. This is known as 'the curse of dimensionality' and was proposed by Bellman in 1961 to describe the exponential growth in combinatorial optimization as the dimension increases [Reference 30].

Many researchers have used different methods such as Principal component analysis (PCA) or Genetic algorithm (GA) to project a higher dimensional feature space onto a lower dimension space. In the current invention, although these methods or similar methods could be implemented, an alternative and simpler method was investigated to reduce the dimensionality of the feature space. We believe that this new approach is beneficial for embedded systems.

We define vector Aj, created by 5th order coefficients of the flexor muscle group (channel1 recording site), and Bj, created by 5th order coefficients of the extensor muscle group (channel2 recording site), both calculated for the jth 0.2-second window:

$$Aj = \{a_{1j}, a_{2j}, a_{3j}, a_{4j}, a_{5j}\} \tag{10}$$

$$Bj = \{b_{1j}, b_{2j}, b_{3j}, b_{4j}, b_{5j}\} \tag{11}$$

The 10-dimentional feature vector was formed as:

$$F_{Aj,Bj} = \{(a_{1j}, a_{2j}, a_{3j}, a_{4j}, a_{5j}), (b_{1j}, b_{2j}, b_{3j}, b_{4j}, b_{5j})\} \tag{12}$$

Preliminary studies showed that AR coefficients change from one movement to another. Therefore, it was expected that the standard deviation among the coefficients could provide a unique signature for each movement.

Standard Deviation

The standard unbiased deviation estimate, S, of a data vector x is given by, $$S = \left(\frac{1}{N-1} \sum_{j=1}^{N} (x_j - \bar{x})^2\right)^{\frac{1}{2}}, \tag{13}$$

where, $$\bar{x} = \frac{1}{N} \sum_{j=1}^{N} x_j \tag{14}$$

and N is the number of elements in the sample. It can be clearly seen that this function always maps N numbers to one number. Therefore, by applying the standard deviation function to Equation (12), the 10-dimensional MMG feature space was converted to a 2-dimensional feature space:

$$F_{stdev(Aj),stdev(Bj)} = (Stdev(a_{1j}, a_{2j}, a_{3j}, a_{4j}, a_{5j}), Stdev(b_{1j}, b_{2j}, b_{3j}, b_{4j}, b_{5j})), \quad (15)$$

where Stdev( . . . ) is the standard deviation using Equation (13).

An Example of MMG-Based System

Figure 9:
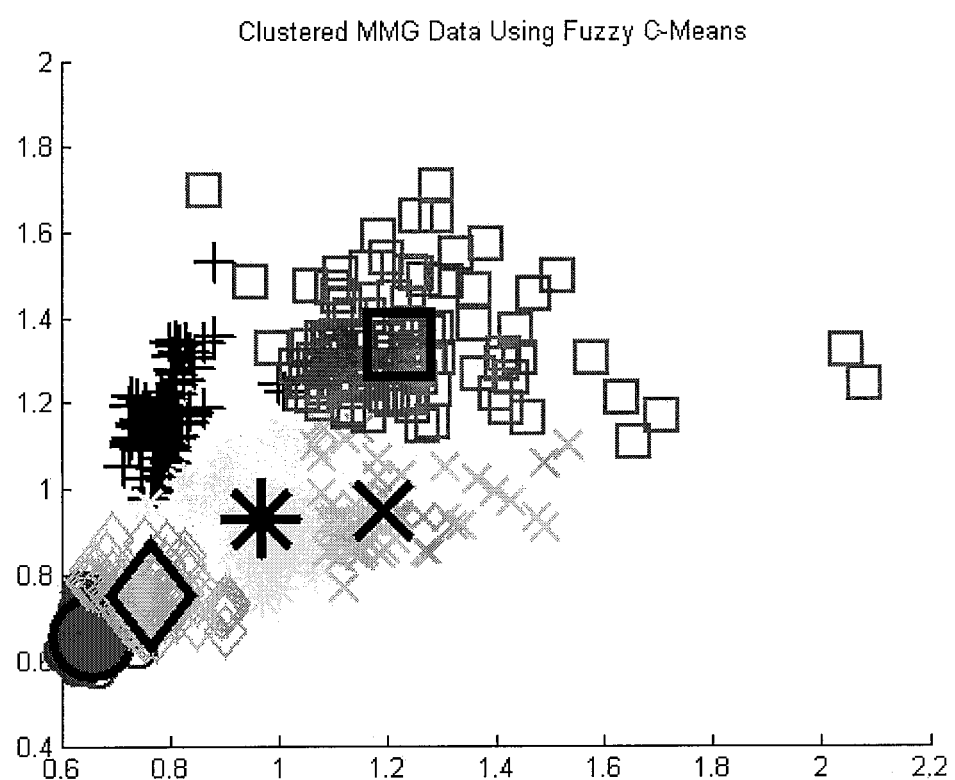
FIG. 9 illustrates the resulting clustered data for an MMG-based system.

Similar to EMG-based system that was described earlier, the raw MMG signals were recorded from two sites on the subject's forearm. Two sets of MMG electrodes were placed on the bulk of the muscles. The MMG signals were filtered at 100 Hz and sampled at 1000 Hz. A 0.2-second window, similar to the window used in EMG system, was used to calculate the features. The user trained the system for two minutes. The features were calculated based on Equation (15). FIG. 9 shows an example of a clustered feature space after the training period. In this example the subject created 6 different movements, and it appears that fuzzy clustering algorithm could clearly identify the clusters associated to different movements. Similar to the EMG-based system, different movements were classified in real-time, based on the user's self-selected intentional movements.

Other Possible Feature Sets

Preliminary studies on MMG signals revealed that the following feature sets could also be used in this invention:

Root-mean-square (RMS) of MMG signals, calculated over a sampling window (i.e. 0.2-second window).

The product of RMS values and the mean/median frequency of the signal, calculated over a sampling window (i.e. 0.2-second window).

In sum, the protocol and the procedure that were earlier described in the EMG-based system can be applied to MMG signals without any restrictions. The only difference between an EMG-based system and MMG-based system is in choice of feature sets. It is believed that the standard deviation of the $5^{th}$ order autoregressive coefficients of MMG signals can create a suitable feature set with acceptable resolution in MMG-based systems. The RMS feature space and the product of RMS and the mean/median frequency may also be used as meaning feature sets.

LIST OF REFERENCES

[1] F. H. Y. Chan, Y.-S. Yang, F. K. Lam, Y.-T. Zhang, and P. A. Parker, "Fuzzy EMG classification for prosthesis control," *IEEE Transactions On Rehabilitation Engineering*, vol. 8, no. 3, pp. 305-311, September 2000.

[2] S. M. ElBasiouny, A. M. El-Bialy, M. F. Taher, A. H. Kandil, and M. E. Rasmy, "A myoelectric prosthesis controller," in *Proceedings of IEEE 29th Annual Bioengineering Conference*, March 2003, pp. 140-141.

[3] B. Karlik, M. O. Tokhi, and M. Alci, "A fuzzy clustering neural network architecture for multifunction upper-limb prosthesis," *IEEE Transactions on Biomedical Engineering*, vol. 50, no. 11, pp. 1255-1261, November 2003.

[4] D. Nishikawa, W. Yu, H. Yokoi, and Y. Kakazu, "On-line learning method for EMG prosthetic hand control," *Electronics and Communications in Japan, Part 3*, vol. 84, no. 10, pp. 1510-1519, November 2001.

[5] K. Englehart, B. Hudgins, and P. A. Parker, "A wavelet-based continuous classification scheme for multifunction myoelectric control," *IEEE Transactions on Biomedical Engineering*, vol. 48, no. 3, March 2001.

[6] D. Peleg, E. Braiman, E. Yom-Tov, and G. F. Inbar, "Classification of finger activation for use in a robotic prosthesis arm," *IEEE Transactions on Neural Systems and Rehabilitation Engineering*, vol. 10, no. 4, pp. 290-293, December 2002.

[7] N. Ma, D. K. Kumar, and N. Pah, "Classification of hand direction using multi-channel electromyography by neural network," in *The Seventh Australian and New Zealand 2001 Intelligent Information Systems Conference*, November 2001, pp. 405-410.

[8] H.-P. Huang, Y.-H. Liu, and C.-S. Wong, "Automatic EMG feature evaluation for controlling a prosthetic hand using supervised feature mining method: an intelligent approach," in *Proceedings of the 2003 IEEE International Conference on Robotics and Automation*, vol. 1, Taipei, Taiwan, September 2003, pp. 220-225.

[9] H.-P. Huang, Y.-H. Liu, L.-W. Liu, and C.-S. Wong, "EMG classification for prehensile postures using cascaded architecture of neural networks with self-organizing maps," in *Proceedings of the 2003 IEEE International Conference on Robotic and Automation*, vol. 1, Taipei, Taiwan, September 2003, pp. 1497-1502.

[10] K. Englehart and B. Hudgins, "A robust, real-time control scheme for multifunction myoelectric control," *IEEE Transactions on Biomedical Engineering*, vol. 50, no. 7, pp. 848-854, July 2003.

[11] K. Englehart, B. Hudgins, and A. D. Chan, "Continuous multifunction myoelectric control using pattern recognition," *Technology and Disability*, vol. 15, pp. 95-103, 2003.

[12] M. Vuskovic and S. Du, "Classification of prehensile EMG patterns with simplified fuzzy ARTMAP networks," in *Proceedings of the 2002 International Joint Conference on Neural Networks, IJCNN '02*, vol. 3, Honolulu, Hi., May 2002, pp. 2539-2544.

[13] Y. Yazama, M. Fukumi, Y. Mitsukura, and N. Akamatsu, "Feature analysis for the EMG signals based on the class distance," in *Proceedings of the 2003 IEEE International Symposium on Computational Intelligence in Robotics and Automation*, vol. 2, Kobe, Japan, July 2003, pp. 860-863.

[14] Y. Matsumura, Y. Mitsukura, M. Fukumi, and N. Akamatsu, "Recognition of EMG signal patterns by neural networks," in *Proceedings of the 9th International Conference on Neural Information Processing*, vol. 2, November 2002, pp. 750-754.

[15] M. Santa-Cruz, R. Riso, and F. Sepulveda, "Optimal selection of time series coefficients for wrist myoelectric control based on intramuscular recordings," in *Proceedings of the 23rd Annual International Conference of the IEEE Engineering in Medicine and Biology Society*, vol. 2, Istanbul, Turkey, October 2001, pp. 1384-1387.

[16] R. Boostani and M. H. Moradi, "Evaluation of the forearm EMG signal features for the control of a prosthetic hand," *Physiological Measurement*, vol. 24, no. 2, pp. 309-319, May 2003.

[17] K. Englehart, B. Hudgins, P. Parker, and M. Stevenson, "Classification of the myoelectric signal using time-frequency based representations," *Medical Engineering & Physics*, vol. 21, no. 6-7, pp. 431-438, July 1999.

[18] X. Zhang, Y. Yang, X. Xu, and M. Zhang, "Wavelet based neuro-fuzzy classification for EMG control," in *IEEE 2002 International Conference on Communications, Circuits and Systems and West Sino Expositions*, vol. 2, July 2002, pp. 1087-1089.

[19] S. E. Hussein and M. H. Granat, "Intention detection using a neuro-fuzzy EMG classifier," *IEEE Engineering in Medicine and Biology Magazine*, vol. 21, no. 6, pp. 123-129, November-December 2002.

[20] J. C. Bezdek, *Pattern Recognition with Fuzzy Objective Function Algorithms*. Plenum Press, New York, 1981.
[21] N. R. Pal and J. C. Bezdek, "On cluster validity for the fuzzy c-means model," *IEEE Transactions on Fuzzy Systems*, vol. 3, no. 3, pp. 370-379, August 1995.
[22] C. J. DeLuca, "The use of surface electromyography in biomechanics," *Journal of applied Biomechanics*, vol. 13, pp. 135-163, 1997.
[23] J. V. Basmajian and C. J. Deluca, Muscles Alive, their functions revealed by electromyography, 5th ed. Williams
[24] B. S. Hudgins, P. A. Parker and R. N. Scott, A new strategy for multifunction myoelectric control, *IEEE Transactions on Biomedical Engineering* 40(1) (1993), 82-94.
[25] A. B. Ajiboye, R. F Weir, A Heuristic Fuzzy Logic Approach to EMG Pattern Recognition for Multifunctional Prosthesis Control, *IEEE Transactions on Neural systems and Rehabilitation Engineering*, Vol. 13, No. 3, September 2005
[26] F. Sebelius, L. Eriksson, H. Holmberg, A. Levinsson, G. Lundborg, N. Danielsen, J. Schouenborg, C. Balkenius, T. Laurell, L. Montelius, *Classification of motor commands using a modified self-organizing feature map*, Medical Engineering & Physics 27 (2005) 403-413
[27] Y. Huang, K. B. Englehart, B. Hudgins, A. D. C. Chan, *A Gaussian Mixture Model Based Classification Scheme for Myoelectric Control of Powered Upper Limb Prostheses*, IEEE TRANSACTIONS ON BIOMEDICAL ENGINEERING, VOL. 52, NO. 11, NOVEMBER 2005
[28] C. Orizio, D. Liberati, C. Locatelli, D. DeGrandis, A. Veicsteinas A. *Surface mechanomyogram reflects muscle fibres twitches summation*, JOURNAL OF BIOMECHANICS 29 (4): 475-481 APRIL 1996
[29] J. G. Proakis and D. G. Manolakis. Digital Signal Processing: Principles, Algorithms and Applications. Prentice Hall, third edition, 1996
[30] D. W. Scott. Multivariate Density Estimation. John Wiley & Sons Inc., New York, 1992

What is claimed is:

1. A computer-implemented method for (i) a user to train at least one computer substantially in real-time by performing a series of randomly-performed, self-selected, intentional muscle movements selected by the user, and (ii) the user to label the muscle movements, comprising:
a user actuating a user-controlled device according to a series of any randomly-performed, self-selected, intentional movements selected by the user;
the at least one computer recording and compiling the user's muscle signals corresponding to the randomly-performed, self-selected, intentional movements of the device, the at least one computer clustering the compiled muscle signals into at least one cluster of signals;
the at least one computer unsupervised-classifying the at least one cluster of signals as at least one non-predetermined function of the user-controlled device, without reference to predetermined classifications of muscle signals; and
after the unsupervised-classifying, the at least one computer accepting user input to label the classified muscle signals to correspond to the at least one function of the user-controlled apparatus.

2. The method of claim 1, wherein, during the moving, recording, and labelling steps, the user is unsupervised.

3. The method of claim 1, wherein, during the moving, recording, and labelling steps, no skin preparation is applied to the skin of the user.

4. The method of claim 1 wherein the device comprises at least one of a prosthesis, a gaming device, a writing apparatus, and a computer input device.

5. The method of claim 1 wherein the muscle signals are recorded at two or more sites on the body of the user.

6. The method of claim 1 whereby the recording and compiling are accomplished by extracting one or more features of the muscle signals.

7. The method of claim 6, wherein the extraction of the one or more features includes calculating at least one of: (i) autoregressive (AR) coefficient values, (ii) short-time Fourier transform (STFT) coefficient values, (iii) wavelet transform (WT) coefficient values, (iv) wavelet packet transform (WPT) coefficient values, and (v) stationary wavelet transform (SWT) coefficient values, associated with the muscle signals.

8. The method of claim 6, whereby the one or more features of the muscle signals are extracted using a feature extractor.

9. The method of claim 6 whereby the extraction of the one or more features includes calculating natural logarithms of root-mean-square values associated with the muscle signals.

10. The method of claim 6 wherein the clustering comprises calculating one or more clusters in association with the one or more features.

11. The method of claim 10 wherein the labelling comprises using a visual display to provide the user real-time feedback for the user to label cluster centers.

12. The method of claim 10 whereby the one or more cluster centers are calculated using a fuzzy c-means clustering algorithm.

13. The method of claim 10 further comprising the step of using the clusters to calculate membership values in association with the one or more features, whereby the membership values are used to classify the muscle signals.

14. The method of claim 13 whereby classification of the muscle signals occurs on a real-time basis.

15. The method of claim 13, wherein the clusters comprise cluster centers, and wherein the step of calculating one or more clusters includes the step of calculating one or more cluster centers, and wherein the step of using the clusters includes the step of using the cluster centers.

16. The method of claim 15, wherein the step of calculating the membership values includes the step of calculating a distance from a cluster center.

17. A computer-implemented method for a user to train at least one computer substantially in real-time by performing a series of randomly-performed, self-selected, intentional muscle movements selected by the user, the method comprising:
enabling a user to actuate a device according to non-predetermined, randomly-performed, intentional movements of the user and selected by the user;
recording and compiling the user's (i) flexor muscle signals and (ii) extensor muscle signals, corresponding to the non-predetermined, randomly-performed, self-selected, intentional movements;
the at least one computer calculating natural logarithms of root-mean-square values associated with the flexor and extensor muscle signals to yield features of the muscle signals;
the at least one computer clustering the flexor and extensor muscle signal features, thereby defining one or more cluster centers corresponding to the flexor and extensor muscle signal features;
the at least one computer calculating cluster membership values by comparing the flexor and extensor muscle signal features and the cluster centers;

the at least one computer unsupervised-classifying one or more clusters as one or more non-predetermined functions of the device, without reference to predetermined classifications of muscle signals; and the at least one computer unsupervised-classifying newly-received flexor and extensor muscle signal features according to the membership values.

18. A system for a user to train at least one computer substantially in real-time by performing a series of randomly-performed, self-selected, intentional muscle movements selected by the user, comprising:

a device operable to record a user's muscle signals in association with the series of randomly-performed, self-selected, intentional muscle movements selected by the user, the device including or being linked to the at least one computer; and the at least one computer programmed to cause the at least one computer to compile and classify the muscle signals by:

recording and compiling the user's muscle signals in association with the series of randomly-performed, self-selected, intentional muscle movements selected by the user;

mapping the muscle signals to the series of randomly-performed, self-selected, intentional muscle movements selected by the user by clustering the muscle signals in accordance with flexor muscle signals and extensor muscle signals into one or more clusters;

unsupervised-classifying the one or more clusters as one or more non-predetermined functions of the device, without reference to predetermined classifications of muscle signals; and periodically re-clustering the muscle signals in accordance with previously-received muscle signals and newly-received muscle signals.

19. The system of claim 18 further comprising a visual display means that provides cues to the user to perform random, self-selected, specific intentional movements selected by the user.

20. The system of claim 18 wherein the device is operable to record the muscle signals at two or more sites on the body of the user.

21. The system of claim 18 wherein the system includes a feature extractor that is operable to generate features in association with the muscle signals.

22. The system of claim 21 whereby the computer program is operable on the computer to (i) cluster the features and (ii) classify the muscle signals according to membership values calculated in relation to cluster centers.

23. The system of claim 22 whereby the computer program is operable on the computer to classify the muscle signals over a window equal to or less than 0.3 seconds.

24. A muscle signal activated apparatus for a user to train at least one computer substantially in real-time by performing a series of randomly-performed, self-selected, intentional movements selected by the user, comprising:

a movable portion of the apparatus that is operable to record a user's muscle signals in association with the randomly-performed, self-selected, intentional movements of the user;

an electronic device linked to the movable portion, the electronic device being operable to define a calibration mode for enabling the user to calibrate the apparatus, said electronic device being operable to:

provide cues to the user to perform the random, self-selected, intentional movements of the user;

record and compile the user's muscle signals in association with the randomly-performed, self-selected, intentional movements;

clustering the compiled muscle signals into at least one cluster of signals; and unsupervised-classifying the at least one cluster of signals as one or more non-predetermined functions of the movable portion, without reference to predetermined classifications of muscle signals.

25. The apparatus of claim 24 wherein the electronic device includes an input means for providing cues to the user, said input means being selected from the group consisting of: one or more buttons, a keypad, a touch screen, a voice recognition system, or any combination thereof.

26. The apparatus of claim 24 wherein the electronic device is operable to:

generate features from the muscles signals using a feature extractor means;

cluster the features thereby defining one or more cluster centers in association with the features;

calculate membership values by comparing the features and the cluster centers; and classify the muscle signals according to the membership values.

27. The apparatus of claim 26 wherein the electronic device includes a feedback means that is operable to enable the user to label the cluster centers according to the randomly-performed, self-selected, intentional movements.

28. The apparatus of claim 26, wherein the electronic device is operable to re-cluster the features based on previously-received muscle signals and newly-received muscle signals.

29. The apparatus as claimed in claim 26, wherein the electronic device includes a controller.

30. The apparatus as claimed in claim 29, wherein the controller includes a control program that cooperates with the controller to perform the operations of the electronic device.

31. A non-transitory computer-readable medium for a user to train at least one computer substantially in real-time by performing a series of randomly-performed, self-selected, intentional muscle movements selected by the user, wherein the computer-readable medium includes instructions operable on the at least one computer to:

provide cues to the user to perform the random, self-selected, intentional movements;

record and compile the muscle signals in association with the randomly-performed, self-selected, intentional movements;

clustering the compiled muscle signals into at least one cluster of signals; and unsupervised-classifying the one or more clusters as one or more non-predetermined functions of the intentional movements, without reference to predetermined classifications of muscle signals.

32. The computer-readable medium of claim 31, wherein the computer-readable medium further includes instructions operable on the at least one computer to re-cluster the features based on previously-received muscle signals and newly-received muscle signals.

33. The computer-readable medium claimed in claim 31, wherein the computer-readable medium further includes instructions operable on the at least one computer to:

generate features from the muscles signals using a feature extractor means;

cluster the features thereby defining one or more cluster centers in association with the features;

calculate membership values by comparing the features and the cluster centers; and classify the muscle signals according to the membership values.

34. The computer-readable medium of claim 31 wherein the computer-readable medium further includes instructions operable on the at least one computer to enable the user to label the cluster centers.

35. The computer-readable medium of claim 34 wherein the computer-readable medium further includes instructions operable on the at least one computer to cue the user to perform specific intentional movements corresponding to the labels.

* * * * *

UNITED STATES PATENT AND TRADEMARK OFFICE
CERTIFICATE OF CORRECTION

PATENT NO. : 8,437,844 B2
APPLICATION NO. : 11/506786
DATED : May 7, 2013
INVENTOR(S) : Kaveh Seyed Momen and Tom Tak Kin Chau Page 1 of 1

It is certified that error appears in the above-identified patent and that said Letters Patent is hereby corrected as shown below:

On the Title page in item (12), Syed Momen et al. should read --Seyed Momen et al.--.

On the Title page in item (75), Kaveh Syed Momen should read --Kaveh Seyed Momen--.

Signed and Sealed this
Second Day of July, 2013

Teresa Stanek Rea
*Acting Director of the United States Patent and Trademark Office*